United States Patent
Savage

(10) Patent No.: US 10,227,376 B2
(45) Date of Patent: Mar. 12, 2019

(54) RADIOLABELED CATIONIC STEROID ANTIMICROBIALS AND DIAGNOSTIC METHODS

(71) Applicant: Paul B. Savage, Mapleton, UT (US)

(72) Inventor: Paul B. Savage, Mapleton, UT (US)

(73) Assignee: BRIGHAM YOUNG UNIVERSITY, Provo, UT (US)

(*) Notice: Subject to any disclaimer, the term of this patent is extended or adjusted under 35 U.S.C. 154(b) by 0 days.

(21) Appl. No.: 14/830,356

(22) Filed: Aug. 19, 2015

(65) Prior Publication Data

US 2016/0052959 A1 Feb. 25, 2016

Related U.S. Application Data

(60) Provisional application No. 62/040,851, filed on Aug. 22, 2014, provisional application No. 62/195,014, filed on Jul. 21, 2015.

(51) Int. Cl.
| | | |
|---|---|---|
| G01N 33/534 | (2006.01) | |
| C07J 43/00 | (2006.01) | |
| A61K 51/04 | (2006.01) | |
| C07J 41/00 | (2006.01) | |
| G01N 33/569 | (2006.01) | |

(52) U.S. Cl.
CPC ......... *C07J 43/003* (2013.01); *A61K 51/0493* (2013.01); *C07J 41/0088* (2013.01); *G01N 33/534* (2013.01); *G01N 33/56911* (2013.01); *G01N 33/56983* (2013.01)

(58) Field of Classification Search
CPC . C07J 43/003; C07J 41/0088; A61K 51/0493; G01N 33/534; G01N 33/56911; G01N 33/56983

USPC .......................................... 552/515; 434/1.45
See application file for complete search history.

(56) References Cited

U.S. PATENT DOCUMENTS

| | | | |
|---|---|---|---|
| 4,248,236 | A | 2/1981 | Linder |
| 4,296,206 | A | 10/1981 | Simons |
| 4,661,341 | A | 4/1987 | Benedict et al. |
| 4,723,950 | A | 2/1988 | Lee |

(Continued)

FOREIGN PATENT DOCUMENTS

| | | |
|---|---|---|
| CN | 101378761 | 3/2009 |
| CN | 102172356 | 9/2011 |

(Continued)

OTHER PUBLICATIONS

U.S. Appl. No. 13/783,007, filed Mar. 1, 2013, Savage.

(Continued)

*Primary Examiner* — Sabiha N Qazi
(74) *Attorney, Agent, or Firm* — Workman Nydegger

(57) ABSTRACT

The disclosure provides compounds, methods, and kits for diagnosis, detection, screening, and imaging of a disease condition (e.g., infection, cancer, tumor, neoplasia), in vitro, ex vivo, and/or in vivo. Certain embodiments include administering a cationic steroid antimicrobial (a "CSA" or "ceragenin"), the CSA including a steroidal backbone and a heterocyclic ring separated from the steroidal backbone by at least 4 atoms (and up to 24 atoms or more), to a subject having or at risk of having a disease condition in an amount effective to diagnose, detect, screen for or image the disease condition in the subject.

26 Claims, 6 Drawing Sheets

(56) References Cited

U.S. PATENT DOCUMENTS

| | | |
|---|---|---|
| 4,842,593 A | 6/1989 | Jordan et al. |
| 4,865,855 A | 9/1989 | Hansen et al. |
| 4,972,848 A | 11/1990 | Di Domenico |
| 5,025,754 A | 6/1991 | Plyler |
| 5,286,479 A | 2/1994 | Garlich et al. |
| 5,310,545 A | 5/1994 | Eisen |
| 5,356,630 A | 10/1994 | Laurencin et al. |
| 5,364,650 A | 11/1994 | Guthery |
| 5,380,839 A | 1/1995 | McCall et al. |
| 5,552,057 A | 9/1996 | Hughes et al. |
| 5,624,704 A | 4/1997 | Darouiche et al. |
| 5,687,714 A | 11/1997 | Kolobow |
| 5,721,359 A | 2/1998 | Dunn et al. |
| 5,763,430 A | 6/1998 | Zasloff |
| 6,117,332 A | 9/2000 | Hatch et al. |
| 6,228,393 B1 | 5/2001 | DiCosmo et al. |
| 6,329,488 B1 | 12/2001 | Terry et al. |
| 6,350,738 B1 | 2/2002 | Savage et al. |
| 6,486,148 B2 | 11/2002 | Savage et al. |
| 6,562,318 B1 | 5/2003 | Filler |
| 6,582,713 B2 | 6/2003 | Newell et al. |
| 6,673,771 B1 | 1/2004 | Greene et al. |
| 6,767,904 B2 | 7/2004 | Savage et al. |
| 6,803,030 B2 * | 10/2004 | De Haen ............ C07J 43/003 424/9.323 |
| 6,803,066 B2 | 10/2004 | Traeder |
| 6,872,303 B2 | 3/2005 | Knapp et al. |
| 6,939,376 B2 | 7/2005 | Shulze et al. |
| 7,226,577 B2 * | 6/2007 | Cappelletti ............ C07K 7/086 424/1.11 |
| 7,282,214 B2 | 10/2007 | Willcox et al. |
| 7,381,439 B2 | 6/2008 | Hilgren et al. |
| 7,598,234 B2 | 10/2009 | Savage et al. |
| 7,611,692 B2 * | 11/2009 | Cappelletti ............ C07K 7/086 424/1.11 |
| 7,659,061 B2 | 2/2010 | Hendl et al. |
| 7,754,705 B2 | 7/2010 | Savage et al. |
| 7,850,947 B2 * | 12/2010 | Cappelletti .......... A61K 49/085 424/1.11 |
| 7,854,941 B2 | 12/2010 | Urban et al. |
| 7,993,903 B2 | 8/2011 | Hayakawa et al. |
| 8,211,879 B2 | 7/2012 | Savage et al. |
| 8,420,050 B2 * | 4/2013 | Cappelletti .......... A61K 49/085 424/1.11 |
| 8,444,954 B2 * | 5/2013 | Cappelletti .......... A61K 49/085 424/1.11 |
| 8,529,681 B1 | 9/2013 | Hibbs et al. |
| 8,623,416 B2 | 1/2014 | Zasloff et al. |
| 8,691,252 B2 | 4/2014 | Savage |
| 8,784,857 B2 | 7/2014 | Savage |
| 8,932,614 B2 | 1/2015 | Savage et al. |
| 8,945,217 B2 | 2/2015 | Savage et al. |
| 8,975,310 B2 | 3/2015 | Savage |
| 9,155,746 B2 | 10/2015 | Genberg et al. |
| 9,161,942 B2 | 10/2015 | Genberg et al. |
| 9,527,883 B2 | 12/2016 | Savage et al. |
| 2002/0091278 A1 | 7/2002 | Savage et al. |
| 2003/0018306 A1 | 1/2003 | Bucay-Couto et al. |
| 2003/0099717 A1 | 5/2003 | Cabrera |
| 2003/0170354 A1 | 9/2003 | Beelman et al. |
| 2004/0009227 A1 | 1/2004 | Yao |
| 2004/0011358 A1 | 1/2004 | Smaldone et al. |
| 2004/0018154 A1 | 1/2004 | Pan |
| 2004/0058974 A1 | 3/2004 | Courtney et al. |
| 2004/0071781 A1 | 4/2004 | Chattopadhyay et al. |
| 2004/0126409 A1 | 7/2004 | Wilcox et al. |
| 2004/0170563 A1 | 9/2004 | Meade |
| 2004/0259445 A1 | 12/2004 | Hilfenhaus et al. |
| 2005/0032765 A1 | 2/2005 | Savage et al. |
| 2005/0075321 A1 | 4/2005 | Ahlem et al. |
| 2005/0244468 A1 | 11/2005 | Huang et al. |
| 2005/0267051 A1 | 12/2005 | Lee et al. |
| 2006/0062742 A1 | 3/2006 | Davis et al. |
| 2006/0269485 A1 | 11/2006 | Friedman et al. |
| 2007/0053788 A1 | 3/2007 | Zhao |
| 2007/0077292 A1 | 4/2007 | Pinsky |
| 2007/0106393 A1 | 5/2007 | Miles et al. |
| 2007/0134292 A1 | 6/2007 | Suokas et al. |
| 2007/0190066 A1 | 8/2007 | Savage et al. |
| 2007/0190067 A1 | 8/2007 | Savage et al. |
| 2007/0190558 A1 | 8/2007 | Savage et al. |
| 2007/0269375 A1 * | 11/2007 | Chen ..................... A61K 51/12 424/1.69 |
| 2008/0124376 A1 | 5/2008 | Pruitt et al. |
| 2008/0174035 A1 | 7/2008 | Winterton |
| 2008/0188819 A1 | 8/2008 | Kloke et al. |
| 2008/0279944 A1 | 11/2008 | Sawhney |
| 2009/0016973 A1 | 1/2009 | Ratcliff et al. |
| 2009/0054295 A1 | 2/2009 | Vicari et al. |
| 2009/0068122 A1 | 3/2009 | Pilch et al. |
| 2009/0099531 A1 | 4/2009 | Griesbach, III |
| 2009/0252781 A1 | 10/2009 | Sawhney et al. |
| 2009/0324517 A1 | 12/2009 | Kline |
| 2010/0022481 A1 | 1/2010 | Wang et al. |
| 2010/0092398 A1 | 4/2010 | Reynolds |
| 2010/0226884 A1 | 9/2010 | Chang et al. |
| 2010/0330086 A1 | 12/2010 | Savage et al. |
| 2011/0091376 A1 * | 4/2011 | Savage ............... A61K 51/0493 424/1.45 |
| 2011/0123624 A1 | 5/2011 | Zasloff |
| 2011/0135742 A1 | 6/2011 | Kim et al. |
| 2011/0230589 A1 | 9/2011 | Maggio et al. |
| 2012/0088733 A1 | 4/2012 | Kim et al. |
| 2012/0107382 A1 | 5/2012 | Savage et al. |
| 2012/0128793 A1 | 5/2012 | Miller et al. |
| 2013/0004586 A1 | 1/2013 | Vachon |
| 2013/0022651 A1 | 1/2013 | Savage |
| 2013/0040265 A1 | 2/2013 | Park et al. |
| 2013/0236619 A1 | 9/2013 | Savage |
| 2013/0280312 A1 | 10/2013 | De Szalay |
| 2013/0280391 A1 | 10/2013 | Savage |
| 2014/0107090 A1 * | 4/2014 | Beus ..................... A61K 31/575 514/182 |
| 2014/0194401 A1 | 7/2014 | Genberg et al. |
| 2014/0219914 A1 * | 8/2014 | Govindan ............ A61K 31/454 424/1.53 |
| 2014/0271761 A1 | 9/2014 | Savage et al. |
| 2014/0274913 A1 | 9/2014 | Savage et al. |
| 2014/0305461 A1 | 10/2014 | Pimenta et al. |
| 2014/0315873 A1 | 10/2014 | Beus et al. |
| 2014/0336131 A1 | 11/2014 | Savage et al. |
| 2014/0363780 A1 | 12/2014 | Vazquez et al. |
| 2014/0369941 A1 | 12/2014 | Vazquez et al. |
| 2015/0093423 A1 | 4/2015 | Savage et al. |
| 2015/0110767 A1 | 4/2015 | Savage et al. |
| 2015/0140063 A1 | 5/2015 | Savage |
| 2015/0203527 A1 | 7/2015 | Savage |
| 2015/0239928 A1 | 8/2015 | Savage |
| 2015/0258121 A1 | 9/2015 | Darien et al. |
| 2015/0258122 A1 | 9/2015 | Beus et al. |
| 2015/0258123 A1 | 9/2015 | Savage et al. |
| 2016/0193232 A1 | 3/2016 | Beus et al. |
| 2016/0199390 A1 | 3/2016 | Beus et al. |
| 2016/0311850 A1 | 10/2016 | Savage et al. |
| 2017/0232004 A1 | 8/2017 | Savage et al. |

FOREIGN PATENT DOCUMENTS

| | | |
|---|---|---|
| DE | 1037074 | 8/1958 |
| EP | 0341951 | 11/1989 |
| EP | 1208844 | 5/2002 |
| EP | 1219631 | 7/2002 |
| JP | 02014741 | 1/1990 |
| JP | H0474026 | 11/1992 |
| JP | 06153779 | 6/1994 |
| JP | 07501826 | 2/1995 |
| JP | 09248454 | 9/1997 |
| JP | 2002505292 | 2/2002 |
| JP | 2002255771 | 9/2002 |
| JP | 2002534532 | 10/2002 |
| JP | 2002538093 | 11/2002 |
| JP | 2004506645 | 3/2004 |

(56) References Cited

FOREIGN PATENT DOCUMENTS

| JP | 2010533051 | 10/2010 |
|---|---|---|
| JP | 2010538074 | 12/2010 |
| JP | 2011527702 | 11/2011 |
| JP | 2014500741 | 1/2014 |
| WO | WO 1995024415 | 9/1995 |
| WO | WO9827106 | 6/1998 |
| WO | WO 9827106 | 6/1998 |
| WO | WO 1999044616 | 9/1999 |
| WO | WO 2000042058 | 7/2000 |
| WO | WO 2002014342 | 2/2002 |
| WO | WO2002067979 | 9/2002 |
| WO | WO2003015757 | 2/2003 |
| WO | WO03090799 | 11/2003 |
| WO | WO2004082588 | 9/2004 |
| WO | WO 2004112852 | 12/2004 |
| WO | WO 2007089903 | 8/2007 |
| WO | WO 2007089906 | 8/2007 |
| WO | WO 2007089907 | 8/2007 |
| WO | WO 2007134176 | 11/2007 |
| WO | WO 2008038965 | 4/2009 |
| WO | WO 2009079066 | 6/2009 |
| WO | 2009144708 | 12/2009 |
| WO | WO2010006192 | 1/2010 |
| WO | WO2010036427 | 4/2010 |
| WO | WO2010062562 | 6/2011 |
| WO | WO2011066260 | 6/2011 |
| WO | WO 2011109704 | 9/2011 |
| WO | WO 2012061651 | 5/2012 |
| WO | WO 2013029055 | 2/2013 |
| WO | WO 2013029059 | 2/2013 |
| WO | WO 2013109236 | 7/2013 |
| WO | 2013167743 | 11/2013 |
| WO | 2014062960 | 4/2014 |

OTHER PUBLICATIONS

U.S. Appl. No. 14/694,028, filed Apr. 23, 2015, Beus et al.
U.S. Appl. No. 14/842,582, filed Sep. 1, 2015, Genberg et al.
U.S. Appl. No. 14/848,819, filed Sep. 9, 2015, Genberg et al.
U.S. Appl. No. 14/866,213, filed Sep. 25, 2015, Savage.
U.S. Appl. No. 14/873,013, filed Oct. 1, 2015, Savage et al.
U.S. Appl. No. 14/750,928, filed Jun. 25, 2015, Genberg et al.
U.S. Appl. No. 14/875,953, filed Oct. 6, 2015, Savage.
U.S. Appl. No. 14/926,738, filed Oct. 29, 2015, Vazquez et al.
Alhanout K et al: "Squalamine as an example of a new potent antimicrobial agents class: a critical review.", Current Medicinal Chemistry 2010, vol. 17, No. 32, 2010, pp. 3909-3917.
Atiq-Ur-Rehman Li C et al: "Preparation of Amino Acid-Appended Cholic Acid Derivatives as Sensitizers of Gram-Negative Bacteria", Tetrahedron Letters, Elsevier, Amsterdam, NL, vol. 40, No. 10, Mar. 5, 1999 (Mar. 5, 1999), pp. 1865-1868, XP004155984, ISSN: 0040-4039, DOI: 10.1016/S0040-4039(99)00075-1.
Berge et al., "Pharmaceutical Salts", Journal of Pharmaceutical Sciences, Jan. 1977, vol. 66, No. 1, pp. 1-19.
Bridot et al., "Hybrid Gadolinium Oxide Nanoparticles: Multimodal Contrast Agents for in Vivo Imaging", Journal of American Chemical Society, vol. 129, No. 16, pp. 5076-5084, Mar. 31, 2007.
Britton et al, "Imaging bacterial infection with 99mTc-ciprofloxacin (Infection)", Journal of Clinical Pathology, vol. 55, pp. 817-823, Apr. 6, 2015.
Bucki et al., "Salivary mucins inhibit antibacterial activity of the cathelicidin-derived LL-37 peptide but not the cationic steroid CSA-13", Journal of Antimicrobial Chemotherapy (2008) 62: 329-335, 7 pages.
Chin et al, "Antimicrobial Activities of Ceragenins against Clinical Isolates of Resistant *Staphylococcus aureas*", Antimicrobial Agents and Chemotherapy, vol. 51, No. 4, Apr. 2007, p. 1268-1273.
Chunhong, et al., "Antimicrobial Activities of Amine- and Guanidine-functionalized Cholic Acid Derivatives", Antimicrobial Agents and Chemotherapy, American Society for Microbiology, Washington DC, US, vol. 43, No. 6, Jun. 1999, pp. 1347-1349.

Clara et al., "Preclinical evaluation of magainin-A as a contraceptive antimicrobial agent", Fertility and Sterility 81 (5), pp. 1357-1365, 2004.
Ding, et al., "Origins of cell selectivity of cationic steroid antibiotics", Journal of American Chemical Society, Oct. 2004, pp. 13642-13648.
Fritsch et al, "In Vitro Activity of Nine Developmental Cationic Steroid Compounds (Ceragenins) against Clinical Isolates of Clostridium difficile", The 46th Interscience Conference on Antimicrobial Agents and Chemotherapy, Sep. 27, 2006, pp. 1-1.
Guan et al: "Preparation and Characterization of Cholic Acid-Derived Antimicrobial Agents with Controlled Stabilities", Organic Letters, American Chemical Society, US, vol. 2, No. 18, Sep. 7, 2000 (Sep. 7, 2000), pp. 2837-2840.
Guan et al: "Supporting Information: Preparation and Characterization of Cholic Acid-Derived Antimicrobial Agents with Controlled Stabilities", Organic Letters, Aug. 17, 2000 (Aug. 17, 2000), pp. 1-7, XP55017313, Retrieved from the Internet: URL:http://pubs.acs.org/doi/suppl/10.1021/010062704/suppl file/o10062704 sl.pdf.
Howell et al., "Ceragenins: A 1-18, class of Antiviral Compounds to Treat Orthopox Infections", Journal of Investigative Dermatology, vol. 129, No. 11, Jun. 11, 2009, pp. 2688-2675.
Isogai E et al: "Ceragenin CSA-13 exhibits antimicrobial activity against cariogenic and periodontopathic bacteria", Oral Microbiology and Immunology, vol. 24, No. 2, Apr. 2009 (Apr. 2009), pp. 170-172.
International Search Report for PCT Application No. PCT/US2009/047485 dated Feb. 17, 2010.
International Search Report for PCT Application No. PCT/US2011/059225 dated Jan. 31, 2012.
International Search Report for PCT Application No. PCT/US2012/047750, dated Oct. 5, 2012.
International Search Report for PCT Application No. PCT/US2012/055244 dated Dec. 5, 2012.
International Search Report for PCT Application No. PCT/US2012/055248 dated Feb. 14, 2013.
International Search Report for PCT Application No. PCT/US2013/038090, dated Jul. 24, 2013.
International Search Report for PCT Application No. PCT/US2014/034986 dated Aug. 28, 2014.
International Search Report for PCT Application No. PCT/US2013/065510 dated Apr. 30, 2015.
International Search Report for PCT Application No. PCT/US2015/020166 dated Sep. 2, 2015.
International Search Report for PCT Application No. PCT/US2015/038029 dated Sep. 29, 2015.
Lai, et al., "Controlled Released of a Bactericidal Ceragenin-Polymer Conjugate", Sep. 27, 2006, p. 1, 46th Annual Interscience Conference on Antimicrobial Agents and Chemotherapy.
Leszczynska et al., "Potential of ceragenin CSA-13 and its mixture with pluronic F-127 as treatment of topical bacterial infections", Journal of Applied Microbiology, vol. 110, No. 1, Oct. 21, 2010, pp. 229-238.
Perry et al., "Assessing peri-implant tissue infection prevention in a percutaneous model", Journal of Biomedical Materials Research Part B: Applied Biomaterials, vol. 02B, Nov. 19, 2009, pp. 397-408.
Pitten F-A, et al., "Efficacy of Cetylpyridinium Chloride Used as Oropharyngeal Antiseptic" Arzenimittel Forschung. Drug Research, ECV Editio Cantor Verlag, Aulendorf, DE, vol. 51, No. 7, Jan. 1, 2001, pp. 588-595.
Savage, et al., "Antibacterial Activities of Thin Films Containing Ceragenins", Microbial Surfaces: Structure, Interactions and Reactivity, ACS, May 30, 2008, pp. 65-78.
Paul B. Savage, et al: "Antibacterial Properties of cationic steroid antibiotics", FEMS Microbiology Letters, vol. 217, Nov. 2002, pp. 1-7.
Savage et al, "Thin Films Containing Ceragenins Prevent Biofilm Formation on Endotracheal Tubes", 9th International Federation of Infection Control Congress, Oct. 14, 2008, pp. 1-1.
P. B. Savage, et al., "Use of a Ceragenin-Based Coating to Prevent Bacterial Colonization of Urinary Catheters", 48th Annual Interscience Conference on Anti-Microbial Agents & Chemotherapy, Oct. 26, 2008, pp. 1-1.

(56) References Cited

OTHER PUBLICATIONS

Shi et al., "Multi-center randomized double-blind clinical trial on efficacy of a mouthwash containing 0.1% cetylpiridinium chloride on gingivitis and plaque and its safety", Chinese Journal of Evidence-Based Medicine (Sep. 2003, vol. 3, No. 3, pp. 171-177).
Sinclair et al., "Development of a broad spectrum polymer-released antimicrobial coating for the prevention of resistant strain bacterial infections", Journal of Biomedical Materials Research Part A, vol. 100A, No. 10, May 24, 2012, pp. 2732-2738.
Steeneveld et al., "Cow-specific treatment of clinical mastitis: an economic approach", Journal of Dairy Science vol. 94, Jan. 2011, pp. 174-188.
Suzuki et al., "Molecular Genetics of Plant Sterol Backbone Synthesis", 2007; Lipids; 42: 47-54.
Van Bambeke et al: "The bacterial envelope as a target for novel anti-MRSA antibiotics", Trends in Pharmacological Sciences, Elsevier, Haywarth, GB, vol. 29, No. 3, Feb. 11, 2008 (Feb. 11, 2008), pp. 124-134.
Van Den Bogaard et al., "Antibiotic Usage in Animals: Impact on Bacterial Resistance and Public Health"; 1999; Drugs; 58 (4): 589-607.
Xin-Zhong Lai et al., "Ceragenins: Cholic Acid-Based Mimics of Antimicrobial peptides", Account of Chemical Research vol. 41, No. 10, Oct. 21, 2008, pp. 1233-1240.
Yin, et al., "Antiangiogenic Treatment Delays Chondrocyte Maturation and Cone Formation During Lim Skeletogenesis", Journal of Bone and Mineral Research, American Society for Bone and Mineral Research, New York, NY, US, vol. 17, No. 1, Jan. 1, 2002.
Zanger et al., "Structure-Activity Relationship and Drug Design", Remington's Pharmaceutical Sciences, Chapter 27, 16th Edition, 1980, pp. 420-425.
U.S. Appl. No. 15/895,848, filed Feb. 13, 2018, Genberg et al.
U.S. Appl. No. 15/926,534, filed Mar. 20, 2018, Savage.
U.S. Appl. No. 15/926,577, filed Mar. 20, 2018, Savage et al.
BASF, Pluronic® Block Copolymer NF Grades (Poloxamer NF Grades), Technical Bulletive (2004).
Belikov V.G., Pharameutical Chemistry, M., Higher School, 1993, p. 43-47.
Bush, "Staphylococcal Infections", Merck Manuals Professional Edition, http://www.merckmanuals.com/professional/infectious-diseases/gram-positive-cocci/staphylococcal-infections.
Cipolla et al., "Inhaled antibiotics to treat lung infection", Pharm Pat Anal., Sep. 2013.
Dennison et al., "Anticancer α-Helical Peptides and Structure/Function Relationships Underpinning their Interactions with Tumour Cell Membranes", Current Protein and Peptide Science, 2006, 7, No. 6, pp. 1-13.
Derakhshandeh et al., "Thermosensitive Pluronic hydrogel: prolonged injectable formulation for drug abuse", Drug Design, Development and Therapy, 2010, 255-262.
Elder et al., "The Utility of Sulfonate Salts in Drug Development", Journal of Pharmaceutical Sciences 99(7): 2948-2961.
Food definition, Merriam Webster, https://www.merriam-webster.com/dictionary/food, Accessed Feb. 12, 2018.
Huang L. et al.: "Synthesis and characterization of organometallic rhenium(I) and technetium(I) bile acid complexes" Journal of organometallic chemistry, Elsevier-Sequoia S.A. Lausanne, CH, col. 694, No. 20, Sep. 15, 2009, pp. 3247-3253.
Jones et al, "Physicochemical Characterization of Hexetidine-Impregnated Endotracheal Tube Poly(Vinyl Chloride) and Resistance to Adherence of Respiratory Bacterial Pathogens", Pharmaceutical Research 19(6): 818-824.
Journal of Ocular Pharmacology and Therapeutics, vol. 27, Issue 1, Table of Contents (Mary Ann Liebert, Inc. publishers), Retrieved from internet <URL:http://online.libertpub.com/toc/jop/27/1>, Downloaded Dec. 1, 2017, 5 pages.
K. Leszczynska et al., "Antibacterial activity of the human host defence peptide LL-37 and selected synthetic cationic lipids against bacteria associated with oral and upper respiratory tract infections", Journal of Antimicrobial Chemotherapy Advance Access, Published Nov. 7, 2012.
Louw et al., "Recueil des Travaux Chimiques des Pays-Bas et la Belgique", vol. 73, pp. 667-676, 1954.
Papo et al., "Host peptides as new weapons in cancer treatment", CMLS Cell. Mol. Life Sci. 62 (2005), 784-790.
Polat et al., "In Vitro Amoebicidal Activity of a Ceragenin, Cationic Steroid Antibiotic-13, Against Acanthamoeba castellanii and Its Cytotoxic Potential", Journal of Ocular Pharmacology and Therapeutics, vol. 27, No. 1, 2011.
Pycock, "The Dirty Mare", https://www.equine-reproduction.com/articles/DirtyMare.shtml, 2003.
Survey Research on Behcet's Disease, 2005 to 2007 Comprehensive Survey Reports, 2008, pp. 34-39.
U.S. Appl. No. 15/934,534, filed Mar. 23, 2018, Savage.
Piktel et al. Sporicidal Activity of Ceragenin CSA-13 Against Bacillus Subtillis, Scientific Reports, vol. 7, Mar. 15, 2017 [retrieved on Apr. 24, 2018. Retrieved from the internet: <URL: https://www.nature.com/articles/srep44452.pdf> Entire Document.
U.S. Appl. No. 15/135,969, filed Apr. 22, 2016, Savage et al.
U.S. Appl. No. 15/270,876, filed Sep. 20, 2016, Genberg, et al.
U.S. Appl. No. 15/333,514, filed Oct. 25, 2016, Vazquez, et al.
U.S. Appl. No. 15/454,135, filed Mar. 9, 2017, Savage et al.
U.S. Appl. No. 15/406,667, filed Jan. 16, 2017, Savage.
U.S. Appl. No. 15/481,884, filed Apr. 7, 2017, Savage.
Press release (Ceragenix Pharmaceuticals, Wayne State University, Brigham Young University, Systemic Anti-Infectives, Preclinical Title—Ceragenin™ Compound demonstrates potent activity multidrug resistant bacterial strains of Pseudomonas, Denver, Co-Published Dec. 20, 2007).
U.S. Appl. No. 13/763,007, filed Mar. 1, 2013, Final Office Action dated Nov. 27, 2015.
International Search Report for PCT Application No. PCT/US2015/046412 dated Dec. 1, 2015.

\* cited by examiner

Kidney slices of CD-1 mice at 2 h *p.i.*

RADIOLABELED CATIONIC STEROID ANTIMICROBIALS AND DIAGNOSTIC METHODS

CROSS-REFERENCE TO RELATED APPLICATIONS

This Application claims the benefit of U.S. Provisional Application No. 62/040,851, filed Aug. 22, 2014, and also U.S. Provisional Application No. 62/195,014, filed Jul. 21, 2015, the disclosures of which are incorporated herein in their entirety.

BACKGROUND

1. Field of Invention

The present disclosure relates to radiolabeled cationic steroid antimicrobials (CSAs) and to diagnostic, detection, screening, and imaging methods using radiolabeled CSAs.

2. Related Technology

Antimicrobial peptides are found in organisms ranging from mammals to amphibians to insects to plants. The ubiquity of antimicrobial peptides has been used as evidence that these compounds do not readily engender bacterial resistance. In addition, considering the varied sequences of antimicrobial peptides among diverse organisms, it is apparent that they have evolved independently multiple times. Thus, antimicrobial peptides appear to be one of "Nature's" primary means of controlling bacterial growth. For example, endogenous antimicrobial peptides, such as the human cathelicidin LL-37, play key roles in innate immunity. LL-37 is found in airway mucus and is believed to be important in controlling bacterial growth in the lung. However, clinical use of antimicrobial peptides presents significant issues including the relatively high cost of producing peptide-based therapeutics, the susceptibility of peptides to proteases generated by the host and by bacterial pathogens, and deactivation of antimicrobial peptides by proteins and DNA in lung mucosa.

An attractive means of harnessing the antibacterial activities of antimicrobial peptides without the issues delineated above is to develop non-peptide mimics of antimicrobial peptides that display similar broad-spectrum antibacterial activity utilizing the same or similar mechanism of action. Non-peptide mimics would offer lower-cost synthesis and potentially increased stability to proteolytic degradation. In addition, control of water solubility and charge density may be used to control association with proteins and DNA in lung mucosa.

With over 1,600 examples of known antimicrobial peptides, it is possible to categorize the structural features common to them. While the primary sequences of these peptides vary substantially, morphologies adopted by a vast majority are similar. Those that adopt helix conformations juxtapose hydrophobic side chains on one face of the helix with cationic (positively charged) side chains on the opposite side. Similar morphology is found in antimicrobial peptides that form beta sheet structures: hydrophobic side chains on one face of the sheet and cationic side chains on the other. See FIG. 9.

Examples of small molecule, non-peptide mimics of antimicrobial peptides, include steroidal compounds known as "ceragenins" or "CSAs," which can reproduce the amphiphilic morphology in antimicrobial peptides.

BRIEF SUMMARY

Disclosed herein are compounds, methods, and kits for diagnosis, detection, screening, and imaging of a disease condition (e.g., infection, cancer, tumor, neoplasia), in vitro, ex vivo, and/or in vivo. Certain embodiments include administering a detectably labelled cationic steroid antimicrobial ("CSA" or "ceragenin"), the detectably labelled CSA including a steroidal backbone and a heterocyclic ring separated from the steroidal backbone by at least 4 atoms, to a subject having or at risk of having a disease condition in an amount effective to diagnose, detect, screen for or image the disease condition in the subject.

CSA compounds of the present disclosure provide a number of advantages and benefits. For example, CSA compounds having a heterocyclic ring (e.g., a heterocyclic ring capable of associating with a detectable label) that is spaced apart from the steroidal backbone of the CSA by at least 4 atoms can provide detection functionality (e.g., at the heterocyclic ring) at a location having enough distance from the steroidal backbone of the compound to reduce or eliminate interference (e.g., steric, chemical, and/or ionic) with portions of the compound that associate with and/or bind to a disease condition.

One or more embodiments of detectably labelled CSA compounds can also include a urea linkage —N—(C=O)—N—, positioned between the steroidal backbone and the heterocyclic ring. Such embodiments can provide further separation between the heterocyclic ring (and the corresponding detection functionality of the molecule) and the rest of the CSA closer to the steroidal backbone of the CSA (and the corresponding disease condition binding functionality of the molecule). For example, the urea linkage can serve to offset the heterocyclic ring and any substituted portions and/or tethering portions of the heterocyclic ring form the steroidal backbone or from a group extending from the steroidal backbone to which the urea linkage is coupled to.

In some embodiments, a method of the disclosure includes administering a detectably labeled CSA to the subject under conditions whereby the labeled CSA can bind to a disease condition, and detecting the labeled CSA in the subject to ascertain the presence or absence of a disease condition, thereby detecting the disease condition, or diagnosing the subject as having or not having a disease condition. In an additional embodiment, a method of the disclosure includes administering a detectably labeled CSA to the subject under conditions whereby the labeled CSA can bind to a disease condition, and imaging the labeled CSA in the subject to ascertain the presence or absence of a disease condition.

The disclosed methods include, among other things, in vitro, ex vivo and/or in vivo methods. Subjects can be contacted with, administered, or delivered a compound (e.g., one or more CSAs) in order to diagnose, detect, screen for or image a disease condition. A sample, such as a biological sample, can be contacted with, administered, or delivered a compound (e.g., one or more CSAs) in order to diagnose, detect, screen for or image a disease condition.

BRIEF DESCRIPTION OF THE DRAWINGS

To further clarify the above and other advantages and features of the present disclosure, a more particular description of the disclosure will be rendered by reference to specific embodiments thereof which are illustrated in the appended drawings. It is appreciated that these drawings depict only illustrated embodiments of the disclosure and are therefore not to be considered limiting of its scope. Embodiments of the disclosure will be described and explained with additional specificity and detail through the use of the accompanying drawings in which.

DETAILED DESCRIPTION

Figure 1:
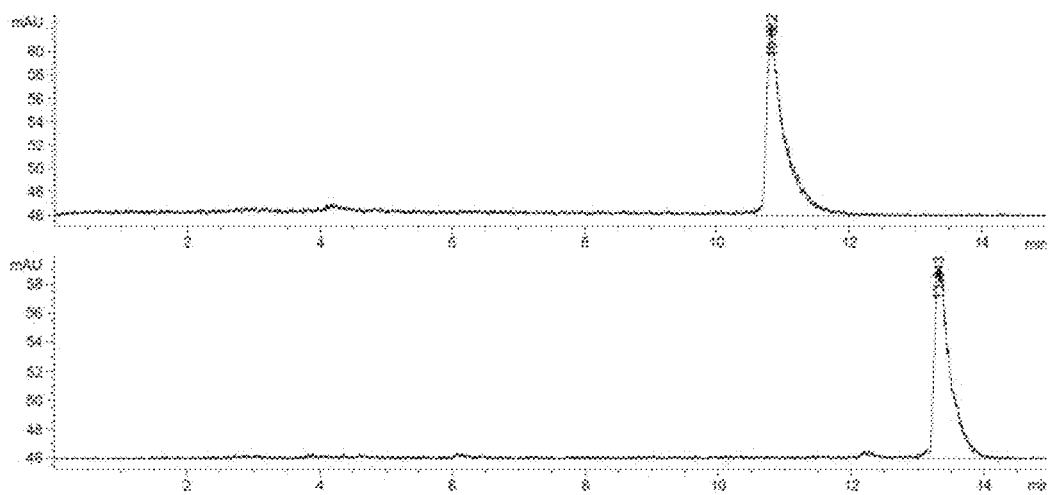
FIG. 1 illustrates shows chromatograms showing the results of labeling a CSA-150 and a CSA-151 compound with a $^{64}$Cu label.

The present disclosure is directed to compounds, methods, and kits for diagnosis, detection, screening, and imaging of a disease condition (e.g., infection, cancer, tumor, neoplasia), in vitro, ex vivo, and/or in vivo. Certain embodiments include administering a cationic steroid antimicrobial (a "CSA" or "ceragenin"), the CSA including a steroidal backbone and a heterocyclic ring separated from the steroidal backbone by at least 4 atoms, to a subject having or at risk of having a disease condition in an amount effective to diagnose, detect, screen for or image the disease condition in the subject. Certain embodiments include CSA compounds capable of detectable label functionality and disease condition binding functionality.

Definitions

The term "contact" and grammatical variations thereof means the subject or a sample is given or delivered a CSA under conditions allowing a physical interaction between the CSA and an infection in vitro, ex vivo and in vivo. The term "administering" includes delivery to a subject in which the CSA can physically interact with an infection in vitro, ex vivo and in vivo.

It is understood that, in any compound described herein having one or more chiral centers, if an absolute stereochemistry is not expressly indicated, then each center may independently be of R-configuration or S-configuration or a mixture thereof. Thus, the compounds provided herein may be enantiomerically pure, enantiomerically enriched, racemic mixture, diastereomerically pure, diastereomerically enriched, or a stereoisomeric mixture. In addition it is understood that, in any compound described herein having one or more double bond(s) generating geometrical isomers that can be defined as E or Z, each double bond may independently be E or Z a mixture thereof.

Likewise, it is understood that, in any compound described, all tautomeric forms are also intended to be included.

It is to be understood that where compounds disclosed herein have unfilled valencies, then the valencies are to be filled with hydrogens or isotopes thereof, e.g., hydrogen-1 (protium) and hydrogen-2 (deuterium).

It is understood that the compounds described herein can be labeled isotopically. Substitution with isotopes such as deuterium may afford certain therapeutic advantages resulting from greater metabolic stability, such as, for example, increased in vivo half-life or reduced dosage requirements. Each chemical element as represented in a compound structure may include any isotope of said element. For example, in a compound structure a hydrogen atom may be explicitly disclosed or understood to be present in the compound. At any position of the compound that a hydrogen atom may be present, the hydrogen atom can be any isotope of hydrogen, including but not limited to hydrogen-1 (protium) and hydrogen-2 (deuterium). Thus, reference herein to a compound encompasses all potential isotopic forms unless the context clearly dictates otherwise.

Unless otherwise indicated, all numbers expressing quantities of ingredients, reaction conditions, and so forth used in the specification and claims are to be understood as being modified in all instances by the term "about" Accordingly, unless indicated to the contrary, the numerical parameters set forth in the specification and attached claims are approximations that may vary depending upon the desired properties sought to be obtained by the present embodiments. At the very least, and not as an attempt to limit the application of the doctrine of equivalents to the scope of the claims, each numerical parameter should be construed in light of the number of significant digits and ordinary rounding approaches.

Notwithstanding that the numerical ranges and parameters setting forth the broad scope of the embodiments are approximations, the numerical values set forth in the specific examples are reported as precisely as possible. Any numerical value, however, inherently contains certain errors necessarily resulting from the standard deviation found in their respective testing measurements. Every numerical range given throughout this specification and claims will include every narrower numerical range that falls within such broader numerical range, as if such narrower numerical ranges were all expressly written herein. Where a range of values is provided, it is understood that the upper and lower limit, and each intervening value between the upper and lower limit of the range is encompassed within the embodiments.

As used herein, any "R" group(s) such as, without limitation, $R_1$, $R_2$, $R_3$, $R_4$, $R_5$, $R_6$, $R_7$, $R_8$, $R_9$, $R_{10}$, $R_{11}$, $R_{12}$, $R_{13}$, $R_{14}$, $R_{15}$, $R_{16}$, $R_{17}$, and $R_{18}$ represent substituents that can be attached to the indicated atom. Unless otherwise specified, an R group may be substituted or unsubstituted.

A "ring" as used herein can be heterocyclic or carbocyclic. The term "saturated" used herein refers to a ring having each atom in the ring either hydrogenated or substituted such that the valency of each atom is filled. The term "unsaturated" used herein refers to a ring where the valency of each atom of the ring may not be filled with hydrogen or other substituents. For example, adjacent carbon atoms in the fused ring can be doubly bound to each other. Unsaturation can also include deleting at least one of the following pairs and completing the valency of the ring carbon atoms at these deleted positions with a double bond, such as $R_5$ and $R_9$; $R_8$ and $R_{10}$; and $R_{13}$ and $R_{14}$.

Whenever a group is described as being "substituted" that group may be substituted with one, two, three or more of the indicated substituents, which may be the same or different, each replacing a hydrogen atom. If no substituents are indicated, it is meant that the indicated "substituted" group may be substituted with one or more group(s) individually and independently selected from alkyl, alkenyl, alkynyl, cycloalkyl, cycloalkenyl, cycloalkynyl, acylalkyl, alkoxyalkyl, aminoalkyl, amino acid, aryl, heteroaryl, heterocyclyl, aralkyl, heteroaralkyl, (heterocyclyl)alkyl, hydroxy, protected hydroxyl, alkoxy, aryloxy, acyl, mercapto, alkylthio, arylthio, cyano, halogen (e.g., F, Cl, Br, and I), thiocarbonyl, O-carbamyl, N-carbamyl, O-thiocarbamyl, N-thiocarbamyl, C-amido, N-amido, S-sulfonamido, N-sulfonamido, C-carboxy, protected C-carboxy, O-carboxy, isocyanato, thiocyanato, isothiocyanato, nitro, oxo, silyl, sulfenyl, sulfinyl, sulfonyl, haloalkyl, haloalkoxy, trihalomethanesulfonyl, trihalomethanesulfonamido, an amino, a mono-substituted amino group and a di-substituted amino group, $R_aO(CH_2)_m$ O—, $R_b(CH_2)_nO$—, $R_cC(O)O(CH_2)_pO$—, and protected derivatives thereof. The substituent may be attached to the group at more than one attachment point. For example, an aryl group may be substituted with a heteroaryl group at two attachment points to form a fused multicyclic aromatic ring system. Biphenyl and naphthalene are two examples of an aryl group that is substituted with a second aryl group.

As used herein, "$C_a$" or "$C_a$ to $C_b$" in which "a" and "b" are integers refer to the number of carbon atoms in an alkyl, alkenyl or alkynyl group, or the number of carbon atoms in the ring of a cycloalkyl, cycloalkenyl, cycloalkynyl, aryl, heteroaryl or heterocyclyl group. That is, the alkyl, alkenyl, alkynyl, ring of the cycloalkyl, ring of the cycloalkenyl, ring of the cycloalkynyl, ring of the aryl, ring of the heteroaryl or ring of the heterocyclyl can contain from "a" to "b", inclusive, carbon atoms. Thus, for example, a "$C_1$ to $C_4$ alkyl" group refers to all alkyl groups having from 1 to 4 carbons, that is, $CH_3$—, $CH_3CH_2$—, $CH_3CH_2CH_2$—, $(CH_3)_2$ CH—, $CH_3CH_2CH_2CH_2$—, $CH_3CH_2CH(CH_3)$— and $(CH_3)_3C$—. If no "a" and "b" are designated with regard to an alkyl, alkenyl, alkynyl, cycloalkyl cycloalkenyl, cycloalkynyl, aryl, heteroaryl or heterocyclyl group, the broadest range described in these definitions is to be assumed.

As used herein, "alkyl" refers to a straight or branched hydrocarbon chain that comprises a fully saturated (no double or triple bonds) hydrocarbon group. The alkyl group may have 1 to 25 carbon atoms (whenever it appears herein, a numerical range such as "1 to 25" refers to each integer in the given range; e.g., "1 to 25 carbon atoms" means that the alkyl group may consist of 1 carbon atom, 2 carbon atoms, 3 carbon atoms, etc., up to and including 25 carbon atoms, although the present definition also covers the occurrence of the term "alkyl" where no numerical range is designated). The alkyl group may also be a medium size alkyl having 1 to 15 carbon atoms. The alkyl group could also be a lower alkyl having 1 to 6 carbon atoms. The alkyl group of the compounds may be designated as "$C_4$" or "$C_1$-$C_4$ alkyl" or similar designations. By way of example only, "$C_1$-$C_4$ alkyl" indicates that there are one to four carbon atoms in the alkyl chain, i.e., the alkyl chain is selected from methyl, ethyl, propyl, iso-propyl, n-butyl, iso-butyl, sec-butyl, and t-butyl. Typical alkyl groups include, but are in no way limited to, methyl, ethyl, propyl, isopropyl, butyl, isobutyl, tertiary butyl, pentyl and hexyl. The alkyl group may be substituted or unsubstituted.

As used herein, "alkenyl" refers to an alkyl group that contains in the straight or branched hydrocarbon chain one or more double bonds. The alkenyl group may have 2 to 25 carbon atoms (whenever it appears herein, a numerical range such as "2 to 25" refers to each integer in the given range; e.g., "2 to 25 carbon atoms" means that the alkenyl group may consist of 2 carbon atom, 3 carbon atoms, 4 carbon atoms, etc., up to and including 25 carbon atoms, although the present definition also covers the occurrence of the term "alkenyl" where no numerical range is designated). The alkenyl group may also be a medium size alkenyl having 2 to 15 carbon atoms. The alkenyl group could also be a lower alkenyl having 1 to 6 carbon atoms. The alkenyl group of the compounds may be designated as "$C_4$" or "$C_2$-$C_4$ alkyl" or similar designations. An alkenyl group may be unsubstituted or substituted.

As used herein, "alkynyl" refers to an alkyl group that contains in the straight or branched hydrocarbon chain one or more triple bonds. The alkynyl group may have 2 to 25 carbon atoms (whenever it appears herein, a numerical range such as "2 to 25" refers to each integer in the given range; e.g., "2 to 25 carbon atoms" means that the alkynyl group may consist of 2 carbon atom, 3 carbon atoms, 4 carbon atoms, etc., up to and including 25 carbon atoms, although the present definition also covers the occurrence of the term "alkynyl" where no numerical range is designated). The alkynyl group may also be a medium size alkynyl having 2 to 15 carbon atoms. The alkynyl group could also be a lower alkynyl having 2 to 6 carbon atoms. The alkynyl group of the compounds may be designated as "$C_4$" or "$C_2$-$C_4$ alkyl" or similar designations. An alkynyl group may be unsubstituted or substituted.

As used herein, "aryl" refers to a carbocyclic (all carbon) monocyclic or multicyclic aromatic ring system (including fused ring systems where two carbocyclic rings share a chemical bond) that has a fully delocalized pi-electron system throughout all the rings. The number of carbon atoms in an aryl group can vary. For example, the aryl group can be a $C_6$-$C_{14}$ aryl group, a $C_6$-$C_{10}$ aryl group, or a $C_6$ aryl group (although the definition of $C_6$-$C_{10}$ aryl covers the occurrence of "aryl" when no numerical range is designated). Examples of aryl groups include, but are not limited to, benzene, naphthalene and azulene. An aryl group may be substituted or unsubstituted.

As used herein, "aralkyl" and "aryl(alkyl)" refer to an aryl group connected, as a substituent, via a lower alkylene group. The aralkyl group may have 6 to 20 carbon atoms (whenever it appears herein, a numerical range such as "6 to 20" refers to each integer in the given range; e.g., "6 to 20 carbon atoms" means that the aralkyl group may consist of 6 carbon atom, 7 carbon atoms, 8 carbon atoms, etc., up to and including 20 carbon atoms, although the present definition also covers the occurrence of the term "aralkyl" where no numerical range is designated). The lower alkylene and aryl group of an aralkyl may be substituted or unsubstituted. Examples include but are not limited to benzyl, 2-phenylalkyl, 3-phenylalkyl, and naphthylalkyl.

"Lower alkylene groups" refer to a $C_1$-$C_{25}$ straight-chained alkyl tethering groups, such as —$CH_2$— tethering groups, forming bonds to connect molecular fragments via their terminal carbon atoms. Examples include but are not limited to methylene (—$CH_2$—), ethylene (—$CH_2CH_2$—), propylene (—$CH_2CH_2CH_2$—), and butylene (—$CH_2CH_2CH_2CH_2$—). A lower alkylene group can be substituted by replacing one or more hydrogen of the lower alkylene group with a substituent(s) listed under the definition of "substituted."

As used herein, "cycloalkyl" refers to a completely saturated (no double or triple bonds) mono- or multi-cyclic hydrocarbon ring system. When composed of two or more rings, the rings may be joined together in a fused fashion. Cycloalkyl groups can contain 3 to 10 atoms in the ring(s) or 3 to 8 atoms in the ring(s). A cycloalkyl group may be unsubstituted or substituted. Typical cycloalkyl groups include, but are in no way limited to, cyclopropyl, cyclobutyl, cyclopentyl, cyclohexyl, cycloheptyl and cyclooctyl.

As used herein, "cycloalkenyl" refers to a mono- or multi-cyclic hydrocarbon ring system that contains one or more double bonds in at least one ring; although, if there is more than one, the double bonds cannot form a fully delocalized pi-electron system throughout all the rings (otherwise the group would be "aryl," as defined herein). When composed of two or more rings, the rings may be connected together in a fused fashion. A cycloalkenyl group may be unsubstituted or substituted.

As used herein, "cycloalkynyl" refers to a mono- or multi-cyclic hydrocarbon ring system that contains one or more triple bonds in at least one ring. If there is more than one triple bond, the triple bonds cannot form a fully delocalized pi-electron system throughout all the rings. When composed of two or more rings, the rings may be joined together in a fused fashion. A cycloalkynyl group may be unsubstituted or substituted.

As used herein, "alkoxy" or "alkyloxy" refers to the formula —OR wherein R is an alkyl, an alkenyl, an alkynyl, a cycloalkyl, a cycloalkenyl or a cycloalkynyl as defined above. A non-limiting list of alkoxys are methoxy, ethoxy, n-propoxy, 1-methylethoxy (isopropoxy), n-butoxy, iso-butoxy, sec-butoxy and tert-butoxy. An alkoxy may be substituted or unsubstituted.

As used herein, "acyl" refers to a hydrogen, alkyl, alkenyl, alkynyl, aryl, or heteroaryl connected, as substituents, via a carbonyl group. Examples include formyl, acetyl, propanoyl, benzoyl, and acryl. An acyl may be substituted or unsubstituted.

As used herein, "alkoxyalkyl" or "alkyloxyalkyl" refers to an alkoxy group connected, as a substituent, via a lower alkylene group. Examples include alkyl-O-alkyl- and alkoxy-alkyl- with the terms alkyl and alkoxy defined herein.

As used herein, "hydroxyalkyl" refers to an alkyl group in which one or more of the hydrogen atoms are replaced by a hydroxy group. Exemplary hydroxyalkyl groups include but are not limited to, 2-hydroxyethyl, 3-hydroxypropyl, 2-hydroxypropyl, and 2,2-dihydroxyethyl. A hydroxyalkyl may be substituted or unsubstituted.

As used herein, "haloalkyl" refers to an alkyl group in which one or more of the hydrogen atoms are replaced by a halogen (e.g., mono-haloalkyl, di-haloalkyl and tri-haloalkyl). Such groups include but are not limited to, chloromethyl, fluoromethyl, difluoromethyl, trifluoromethyl and 1-chloro-2-fluoromethyl, 2-fluoroisobutyl. A haloalkyl may be substituted or unsubstituted.

The term "amino" as used herein refers to a —NH$_2$ group.

As used herein, the term "hydroxy" refers to a —OH group.

A "cyano" group refers to a "—CN" group.

A "carbonyl" or an "oxo" group refers to a C=O group.

The term "azido" as used herein refers to a —N$_3$ group.

As used herein, "aminoalkyl" refers to an amino group connected, as a substituent, via a lower alkylene group. Examples include H2N-alkyl- with the term alkyl defined herein.

As used herein, "alkylcarboxyalkyl" refers to an alkyl group connected, as a substituent, to a carboxy group that is connected, as a substituent, to an alkyl group. Examples include alkyl-C(=O)O-alkyl- and alkyl-O—C(=O)-alkyl- with the term alkyl as defined herein.

As used herein, "alkylaminoalkyl" refers to an alkyl group connected, as a substituent, to an amino group that is connected, as a substituent, to an alkyl group. Examples include alkyl-NH-alkyl-, with the term alkyl as defined herein.

As used herein, "dialkylaminoalkyl" or "di(alkyl)aminoalkyl" refers to two alkyl groups connected, each as a substituent, to an amino group that is connected, as a substituent, to an alkyl group. Examples include

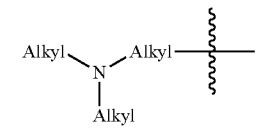

with the term alkyl as defined herein.

As used herein, "alkylaminoalkylamino" refers to an alkyl group connected, as a substituent, to an amino group that is connected, as a substituent, to an alkyl group that is connected, as a substituent, to an amino group. Examples include alkyl-NH-alkyl-NH—, with the term alkyl as defined herein.

As used herein, "alkylaminoalkylaminoalkylamino" refers to an alkyl group connected, as a substituent, to an amino group that is connected, as a substituent, to an alkyl group that is connected, as a substituent, to an amino group that is connected, as a substituent, to an alkyl group. Examples include alkyl-NH-alkyl-NH-alkyl-, with the term alkyl as defined herein.

As used herein, "arylaminoalkyl" refers to an aryl group connected, as a substituent, to an amino group that is connected, as a substituent, to an alkyl group. Examples include aryl-NH-alkyl-, with the terms aryl and alkyl as defined herein.

As used herein, "aminoalkyloxy" refers to an amino group connected, as a substituent, to an alkyloxy group. Examples include H$_2$N-alkyl-O— and H$_2$N-alkoxy- with the terms alkyl and alkoxy as defined herein.

As used herein, "aminoalkyloxyalkyl" refers to an amino group connected, as a substituent, to an alkyloxy group connected, as a substituent, to an alkyl group. Examples include H$_2$N-alkyl-O-alkyl- and H$_2$N-alkoxy-alkyl- with the terms alkyl and alkoxy as defined herein.

As used herein, "aminoalkylcarboxy" refers to an amino group connected, as a substituent, to an alkyl group connected, as a substituent, to a carboxy group. Examples include H$_2$N-alkyl-C(=O)O— and H$_2$N-alkyl-O—C(=O)— with the term alkyl as defined herein.

As used herein, "aminoalkylaminocarbonyl" refers to an amino group connected, as a substituent, to an alkyl group connected, as a substituent, to an amino group connected, as a substituent, to a carbonyl group. Examples include H$_2$N-alkyl-NH—C(=O)— with the term alkyl as defined herein.

As used herein, "aminoalkylcarboxamido" refers to an amino group connected, as a substituent, to an alkyl group connected, as a substituent, to a carbonyl group connected, as a substituent to an amino group. Examples include H$_2$N-alkyl-C(=O)—NH— with the term alkyl as defined herein.

As used herein, "azidoalkyloxy" refers to an azido group connected as a substituent, to an alkyloxy group. Examples include N$_3$-alkyl-O— and N$_3$-alkoxy- with the terms alkyl and alkoxy as defined herein.

As used herein, "cyanoalkyloxy" refers to a cyano group connected, as a substituent, to an alkyloxy group. Examples include NC-alkyl-O— and NC-alkoxy- with the terms alkyl and alkoxy as defined herein.

A "sulfenyl" group refers to an "—SR" group in which R can be hydrogen, alkyl, alkenyl, alkynyl, cycloalkyl, cycloalkenyl, cycloalkynyl, aryl, heteroaryl, heterocyclyl, aralkyl, or (heterocyclyl)alkyl. A sulfenyl may be substituted or unsubstituted.

A "sulfinyl" group refers to an "—S(=O)—R" group in which R can be the same as defined with respect to sulfenyl. A sulfinyl may be substituted or unsubstituted.

A "sulfonyl" group refers to an "SO$_2$R" group in which R can be the same as defined with respect to sulfenyl. A sulfonyl may be substituted or unsubstituted.

An "O-carboxy" group refers to a "RC(=O)O—" group in which R can be hydrogen, alkyl, alkenyl, alkynyl, cycloalkyl, cycloalkenyl, cycloalkynyl, aryl, heteroaryl, heterocyclyl, aralkyl, or (heterocyclyl)alkyl, as defined herein. An O-carboxy may be substituted or unsubstituted.

The terms "ester" and "C-carboxy" refer to a "—C(=O)OR" group in which R can be the same as defined with respect to O-carboxy. An ester and C-carboxy may be substituted or unsubstituted.

A "thiocarbonyl" group refers to a "—C(=S)R" group in which R can be the same as defined with respect to O-carboxy. A thiocarbonyl may be substituted or unsubstituted.

A "trihalomethanesulfonyl" group refers to an "X$_3$CSO$_2$—" group wherein X is a halogen.

An "S-sulfonamido" group refers to a "—SO$_2$N(RARB)" group in which RA and RB can be independently hydrogen, alkyl, alkenyl, alkynyl, cycloalkyl, cycloalkenyl, cycloalkynyl, aryl, heteroaryl, heterocyclyl, aralkyl, or (heterocyclyl)alkyl. An S-sulfonamido may be substituted or unsubstituted.

An "N-sulfonamido" group refers to a "RSO$_2$N(RA)-" group in which R and RA can be independently hydrogen, alkyl, alkenyl, alkynyl, cycloalkyl, cycloalkenyl, cycloalkynyl, aryl, heteroaryl, heterocyclyl, aralkyl, or (heterocyclyl)alkyl. An N-sulfonamido may be substituted or unsubstituted.

An "O-carbamyl" group refers to a "—OC(=O)N(RARB)" group in which RA and RB can be independently hydrogen, alkyl, alkenyl, alkynyl, cycloalkyl, cycloalkenyl, cycloalkynyl, aryl, heteroaryl, heterocyclyl, aralkyl, or (heterocyclyl)alkyl. An O-carbamyl may be substituted or unsubstituted.

An "N-carbamyl" group refers to an "ROC(=O)N(RA)-" group in which R and RA can be independently hydrogen, alkyl, alkenyl, alkynyl, cycloalkyl, cycloalkenyl, cycloalkynyl, aryl, heteroaryl, heterocyclyl, aralkyl, or (heterocyclyl) alkyl. An N-carbamyl may be substituted or unsubstituted.

An "O-thiocarbamyl" group refers to a "—OC(=S)—N(RARB)" group in which RA and RB can be independently hydrogen, alkyl, alkenyl, alkynyl, cycloalkyl, cycloalkenyl, cycloalkynyl, aryl, heteroaryl, heterocyclyl, aralkyl, or (heterocyclyl)alkyl. An O-thiocarbamyl may be substituted or unsubstituted.

An "N-thiocarbamyl" group refers to an "ROC(=S)N(RA)-" group in which R and RA can be independently hydrogen, alkyl, alkenyl, alkynyl, cycloalkyl, cycloalkenyl, cycloalkynyl, aryl, heteroaryl, heterocyclyl, aralkyl, or (heterocyclyl)alkyl. An N-thiocarbamyl may be substituted or unsubstituted.

A "C-amido" group refers to a "—C(=O)N(RARB)" group in which RA and RB can be independently hydrogen, alkyl, alkenyl, alkynyl, cycloalkyl, cycloalkenyl, cycloalkynyl, aryl, heteroaryl, heterocyclyl, aralkyl, or (heterocyclyl) alkyl. A C-amido may be substituted or unsubstituted.

An "N-amido" group refers to a "RC(=O)N(RA)-" group in which R and RA can be independently hydrogen, alkyl, alkenyl, alkynyl, cycloalkyl, cycloalkenyl, cycloalkynyl, aryl, heteroaryl, heterocyclyl, aralkyl, or (heterocyclyl)alkyl. An N-amido may be substituted or unsubstituted.

As used herein, "guanidinoalkyloxy" refers to a guanidinyl group connected, as a substituent, to an alkyloxy group. Examples include

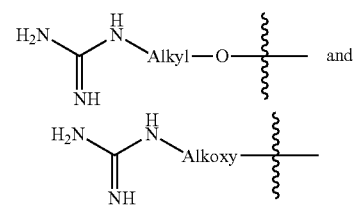

with the terms alkyl and alkoxy as defined herein.

As used herein, "guanidinoalkylcarboxy" refers to a guanidinyl group connected, as a substituent, to an alkyl group connected, as a substituent, to a carboxy group. Examples include

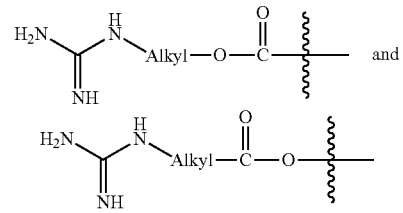

with the term alkyl as defined herein.

As used herein, "quaternary ammonium alkylcarboxy" refers to a quaternized amino group connected, as a substituent, to an alkyl group connected, as a substituent, to a carboxy group. Examples include

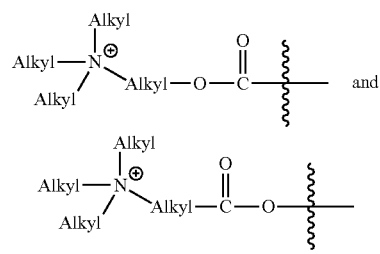

with the term alkyl as defined herein.

The term "halogen atom" or "halogen" as used herein, means any one of the radio-stable atoms of column 7 of the Periodic Table of the Elements, such as, fluorine, chlorine, bromine and iodine.

Where the numbers of substituents is not specified (e.g. haloalkyl), there may be one or more substituents present. For example "haloalkyl" may include one or more of the same or different halogens.

As used herein, the term "amino acid" refers to any amino acid (both standard and non-standard amino acids), including, but not limited to, α-amino acids, β-amino acids, γ-amino acids and δ-amino acids. Examples of suitable amino acids include, but are not limited to, alanine, asparagine, aspartate, cysteine, glutamate, glutamine, glycine, proline, serine, tyrosine, arginine, histidine, isoleucine, leucine, lysine, methionine, phenylalanine, threonine, tryptophan and valine. Additional examples of suitable amino acids include, but are not limited to, ornithine, hypusine, 2-aminoisobutyric acid, dehydroalanine, gamma-aminobutyric acid, citrulline, beta-alanine, alpha-ethyl-glycine, alpha-propyl-glycine and norleucine.

A linking group is a divalent moiety used to link one steroid to another steroid. In some embodiments, the linking group is used to link a first CSA with a second CSA (which may be the same or different). An example of a linking group is ($C_1$-$C_{10}$) alkyloxy-($C_1$-$C_{10}$) alkyl.

The terms "P.G." or "protecting group" or "protecting groups" as used herein refer to any atom or group of atoms that is added to a molecule in order to prevent existing groups in the molecule from undergoing unwanted chemical reactions. Examples of protecting group moieties are described in T. W. Greene and P. G. M. Wuts, *Protective Groups in Organic Synthesis*, 3. Ed. John Wiley & Sons, 1999, and in J. F. W. McOmie, *Protective Groups in Organic Chemistry* Plenum Press, 1973, both of which are hereby incorporated by reference for the limited purpose of disclosing suitable protecting groups. The protecting group moiety may be chosen in such a way, that they are stable to certain reaction conditions and readily removed at a convenient stage using methodology known from the art. A non-limiting list of protecting groups include benzyl; substituted benzyl; alkylcarbonyls and alkoxycarbonyls (e.g., t-butoxycarbonyl (BOC), acetyl, or isobutyryl); arylalkylcarbonyls and arylalkoxy-carbonyls (e.g., benzyloxycarbonyl); substituted methyl ether (e.g. methoxymethyl ether); substituted ethyl ether, a substituted benzyl ether, tetrahydropyranyl ether; silyls (e.g., trimethylsilyl, triethylsilyl, triisopropylsilyl, t-butyldimethylsilyl, tri-iso-propylsilyloxymethyl, [2-(trimethylsilyl)ethoxy]methyl or t-butyldiphenylsilyl); esters (e.g. benzoate ester); carbonates (e.g. methoxymethyl carbonate); sulfonates (e.g. tosylate or mesylate); acyclic ketal (e.g. dimethyl acetal); cyclic ketals (e.g., 1,3-dioxane, 1,3-dioxolanes, and those described herein); acyclic acetal; cyclic acetal (e.g., those described herein); acyclic hemiacetal; cyclic hemiacetal; cyclic dithioketals (e.g., 1,3-dithiane or 1,3-dithiolane); orthoesters (e.g., those described herein) and triarylmethyl groups (e.g., trityl; monomethoxytrityl (MMTr); 4,4'-dimethoxytrityl (DMTr); 4,4',4''-trimethoxytrityl (TMTr); and those described herein). Amino-protecting groups are known to those skilled in the art. In general, the species of protecting group is not critical, provided that it is stable to the conditions of any subsequent reaction(s) on other positions of the compound and can be removed at the appropriate point without adversely affecting the remainder of the molecule. In addition, a protecting group may be substituted for another after substantive synthetic transformations are complete. Clearly, where a compound differs from a compound disclosed herein only in that one or more protecting groups of the disclosed compound has been substituted with a different protecting group, that compound is within the disclosure.

CSA Compounds

By way of background, exemplary CSA compounds are described in U.S. Pat. Nos. 6,350,738, 6,486,148, 6,767,904, 7,598,234, 7,754,705, U.S. Application Nos. 61/786,301, 13/288,892, 61/642,431, 13/554,930, 61/572,714, 13/594,608, 61/576,903, 13/594,612, 13/288,902, 61/605,639, 13/783,131, 61/605,642, 13/783,007, 61/132,361, 13/000,010, 61/534,185, 13/615,244, 61/534,194, 13/615,324, 61/534,205, 61/637,402, 13/841,549, 61/715,277, PCT/US13/37615, 61/749,800, 61/794,721, and 61/814,816, which are incorporated herein by reference. The skilled artisan will recognize the compounds within the generic formulae set forth herein and understand their preparation in view of the references cited herein and the Examples.

The compounds and compositions disclosed herein are optionally prepared as salts. The term "salt" as used herein is a broad term, and is to be given its ordinary and customary meaning to a skilled artisan (and is not to be limited to a special or customized meaning), and refers without limitation to a salt of a compound. In some embodiments, the salt is an acid addition salt of the compound. Salts can be obtained by reacting a compound with inorganic acids such as hydrohalic acid (e.g., hydrochloric acid or hydrobromic acid), sulfuric acid, nitric acid, and phosphoric acid. Salts can also be obtained by reacting a compound with an organic acid such as aliphatic or aromatic carboxylic or sulfonic acids, for example formic acid, acetic acid, propionic acid, glycolic acid, pyruvic acid, malonic acid, maleic acid, fumaric acid, trifluoroacetic acid, benzoic acid, cinnamic acid, mandelic acid, succinic acid, lactic acid, malic acid, tartaric acid, citric acid, ascorbic acid, nicotinic acid, methanesulfonic acid, ethanesulfonic acid, p-toluensulfonic acid, salicylic acid, stearic acid, muconic acid, butyric acid, phenylacetic acid, phenylbutyric acid, valproic acid, 1,2-ethanedisulfonic acid, 2-hydroxyethanesulfonic acid, benzenesulfonic acid, 2-naphthalenesulfonic acid, or naphthalenesulfonic acid. Salts can also be obtained by reacting a compound with a base to form a salt such as an ammonium salt, an alkali metal salt, such as a lithium, sodium or a potassium salt, an alkaline earth metal salt, such as a calcium, magnesium or aluminum salt, a salt of organic bases such as dicyclohexylamine, N-methyl-D-glucamine, tris(hydroxymethyl)methylamine, $C_1$-$C_7$ alkylamine, cyclohexylamine, dicyclohexylamine, triethanolamine, ethylenediamine, ethanolamine, diethanolamine, triethanolamine, tromethamine, and salts with amino acids such as arginine and lysine; or a salt of an inorganic base, such as aluminum hydroxide, calcium hydroxide, potassium hydroxide, sodium carbonate, sodium hydroxide, or the like.

In some embodiments, the salt is a hydrochloride salt. In some embodiments, the salt is a mono-hydrochloride salt, a di-hydrochloride salt, a tri-hydrochloride salt, or a tetra-hydrochloride salt. Additional examples of salts include sulfuric acid addition salts, sulfonic acid addition salts, disulfonic acid addition salts, 1,5-naphthalenedisulfonic acid addition salts, sulfate salts, and bisulfate salts.

In some embodiments, CSA compounds as disclosed herein can be a compound of Formula (I), Formula (II), or salt thereof, having a steroidal backbone:

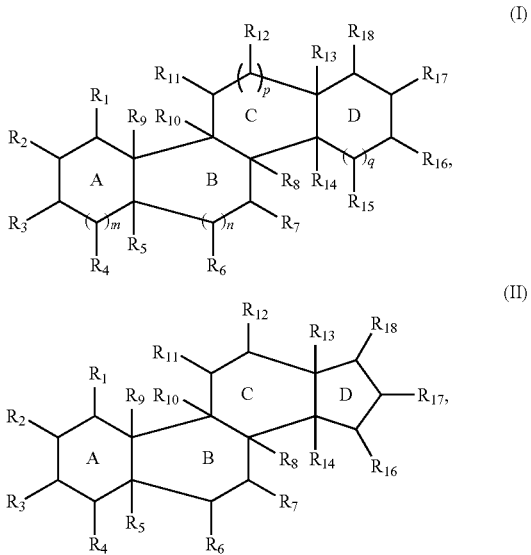

and wherein at least $R_{18}$ of the steroidal backbone includes a heterocyclic ring spaced apart from the steroidal backbone by at least 4 atoms.

In some embodiments, the heterocyclic ring forming part of $R_{18}$ is a macrocyclic chelator capable of complexing with a wide variety of metal ions, such as bi- and trivalent metal ions. For example, the heterocyclic ring can be a triazamacrocyclic ring, such as a 9 to 13 member triazamacrocyclic ring. In some embodiments, the heterocyclic ring of $R_{18}$ may be selected from the group consisting of 1,4,7-triazacyclononane-N,N',N"-triacetic acid (NOTA), 1,4,7-triazacyclodecane-N,N',N"-triacetic acid (DETA), 1,4,8-triazacycloundecane-N,N',N"-triacetic acid (UNTA), 1,5,9-triazacyclododecane-N,N',N"-triacetic acid (DOTRA), 9,10-benzylidene-1,4,7-triazacyclotridecane-N,N',N"-triacetic acid (BUNTA), and derivatives thereof. In other embodiments, the heterocyclic ring of $R_{18}$ can be a tetraazamacrocyclic ring, such as 1,4,7,10-tetraazacyclododecane-1,4,7,10-tetracetic acid (DOTA), or derivatives thereof.

In some embodiments, the heterocyclic ring of $R_{18}$ includes at least 2 heteroatoms. In some embodiments, the heterocyclic ring of $R_{18}$ includes at least 3 or at least 4 heteroatoms. In some embodiments, at least 2 of the heteroatoms are nitrogen atoms. In some embodiments, at least 3 of the heteroatoms are nitrogen atoms. In some embodiments, the heterocyclic ring of $R_{18}$ includes 3 heteroatoms, all of which are nitrogen atoms. In some embodiments, the heterocyclic ring of $R_{18}$ includes 4 heteroatoms, all of which are nitrogen atoms. In some embodiments, the heterocyclic ring of $R_{18}$ omits oxygen, sulfur, phosphorous, and halogen atoms as heteroatoms of the hetocyclic ring.

In some embodiments, $R_{18}$ can include a urea moiety, such as a urea linkage —N—(C═O)—N—, positioned between the steroidal backbone and the heterocyclic ring.

In some embodiments, the heterocyclic ring of $R_{18}$ is spaced apart from the steroidal backbone by 4, 5, 6, 7, 8, 9, 10, 11, 12, 13, 14, 15, 16, 17, 18, 19, 20, 21, 22, 23, or 24 atoms. In some embodiments, the heterocyclic ring of $R_{18}$ is spaced apart from the steroidal backbone by more than 24 atoms. In some embodiments, an alkyl group links the heterocyclic ring with a heteroatom or group containing a heteroatom. The linking group may include one or more ether linkages (e.g. 1-6) between individual alkyl groups (e.g., ethylene groups) in the linking group within the alkyl group (e.g., —C—C—O—C—C—O—C—C—O—C—C—O—).

In some embodiments, $R_{18}$ can include an amide moiety in which the carbonyl group of the amide is positioned between the amido nitrogen of the amide and the heterocyclic ring.

In some embodiments, $R_{18}$ is a heterocyclic ring joined to the rest of the compound by a linkage selected from the group consisting of alkyl, alkyloxyalkyl, alkylcarboxyalkyl, alkylaminoalkyl, alkylaminoalkylamino, alkylaminoalkylamino-alkylamino, aminoalkyl, aryl, arylaminoalkyl, alkenyl, alkynyl, aminoalkyloxy, aminoalkyloxyalkyl, aminoalkylcarboxy, aminoalkylaminocarbonyl, aminoalkylcarboxamido, alkylcarboxamido-alkyl, alkylcarboxamido-alkyloxyalkyl, alkylcarboxamidoalkylcarboxyalkyl, alkylcarboxamido-alkylaminoalkyl, alkylcarboxamido-alkylaminoalkylamino, alkylcarboxamido-alkylaminoalkylamino-alkylamino, alkylcarboxamido-aryl, alkylcarboxamido-arylaminoalkyl, alkylcarboxamido-alkenyl, and alkylcarboxamido-alkynyl.

In some embodiments, the heterocyclic ring of $R_{18}$ is a 5 to 13 member ring. In some embodiments, the heterocyclic ring of $R_{18}$ is an 8 to 12 member ring. In some embodiments, the heterocyclic ring of $R_{18}$ is a 9 to 10 member ring. In some embodiments, the heterocyclic ring of $R_{18}$ is a 9 member ring.

In some embodiments, at least $R_{18}$ can have the following structure:

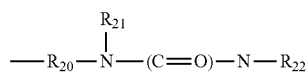

wherein $R_{20}$ is omitted or is an alkyl, alkenyl, alkynyl, or aryl;

$R_{21}$ is selected from the group consisting of hydrogen, $C_1$-$C_{24}$ alkyl, $C_2$-$C_{24}$ alkenyl, $C_2$-$C_{24}$ alkynyl, $C_6$ or $C_{10}$ aryl, 5 to 10 membered heteroaryl, 5 to 10 membered heterocyclyl, $C_7$-$C_{13}$ aralkyl, (5 to 10 membered heteroaryl)-$C_1$-$C_6$ alkyl, $C_3$-$C_{10}$ carbocyclyl, $C_4$-$C_{10}$ (carbocyclyl)alkyl, (5 to 10 membered heterocyclyl)-$C_1$-$C_6$ alkyl, amido, and a suitable amine protecting group; and $R_{22}$ is a 5 to 13 member, 8 to 12 member, or 9 to 10 member heterocyclyl joined to the rest of the compound by a linkage selected from the group consisting of alkyl, -[alkoxy]$_n$-, -[alkoxy]$_n$-alkyl, alkylcarboxamido-alkyl, alkylcarboxamido-[alkoxy]$_n$-, alkylcarboxamido-[alkoxy]$_n$-alkyl, alkylcarboxyalkyl, alkylaminoalkyl, aryl, arylaminoalkyl, alkenyl, and alkynyl, where n is 1 to 10; and wherein each of $R_{20}$, $R_{21}$, and $R_{22}$ may be optionally substituted.

In addition to the foregoing, CSA compounds of Formula (I), Formula (II), and salts thereof can be characterized wherein:

rings A, B, C, and D are independently saturated, or are fully or partially unsaturated, provided that at least two of rings A, B, C, and D are saturated;

m, n, p, and q are independently 0 or 1;

$R_1$ through $R_4$, $R_6$, $R_7$, $R_{11}$, $R_{12}$, $R_{15}$, and $R_{16}$ are independently selected from the group consisting of hydrogen, hydroxyl, a substituted or unsubstituted alkyl, a substituted or unsubstituted hydroxyalkyl, a substituted or unsubstituted alkyloxyalkyl, a substituted or unsubstituted alkylcarboxyalkyl, a substituted or unsubstituted alkylaminoalkyl, a substituted or unsubstituted alkylaminoalkylamino, a substituted or unsubstituted alkylaminoalkylamino-alkylamino, a substituted or unsubstituted aminoalkyl, a substituted or unsubstituted aryl, a substituted or unsubstituted arylaminoalkyl, a substituted or unsubstituted haloalkyl, a substituted or unsubstituted alkenyl, a substituted or unsubstituted alkynyl, oxo, a linking group attached to a second steroid, a substituted or unsubstituted aminoalkyloxy, a substituted or unsubstituted aminoalkyloxyalkyl, a substituted or unsubstituted aminoalkylcarboxy, a substituted or unsubstituted aminoalkylaminocarbonyl, a substituted or unsubstituted aminoalkylcarboxamido, a substituted or unsubstituted di(alkyl)aminoalkyl, $H_2N-HC(Q_5)-C(O)-O-$, $H_2N-HC(Q_5)-C(O)-N(H)-$, a substituted or unsubstituted azidoalkyloxy, a substituted or unsubstituted cyanoalkyloxy, P.G.-HN-HC($Q_5$)-C(O)-O-, a substituted or unsubstituted guanidinoalkyloxy, a substituted or unsubstituted quaternary ammonium alkylcarboxy, and a substituted or unsubstituted guanidinoalkyl carboxy, where $Q_5$ is a side chain of any amino acid (including a side chain of glycine, i.e., H), and P.G. is an amino protecting group; and $R_5$, $R_8$, $R_9$, $R_{10}$, $R_{13}$, $R_{14}$ and $R_{17}$ are independently deleted when one of rings A, B, C, or D is unsaturated so as to complete the valency of the carbon atom at that site, or $R_5$, $R_8$, $R_9$, $R_{10}$, $R_{13}$, $R_{14}$ and $R_{17}$ are independently selected from the group consisting of hydrogen, hydroxyl, a substituted or unsubstituted alkyl, a substituted or unsubstituted hydroxyalkyl, a substituted or unsubstituted alkyloxyalkyl, a substituted or unsubstituted aminoalkyl, a substituted or unsubstituted aryl, a substituted or unsubstituted haloalkyl, a substituted or unsubstituted alkenyl, a substituted or unsubstituted alkynyl, oxo, a linking group attached to a second steroid, a substituted or unsubstituted aminoalkyloxy, a substituted or unsubstituted aminoalkylcarboxy, a substituted or unsubstituted aminoalkylaminocarbonyl, a substituted or unsubstituted di(alkyl)aminoalkyl, $H_2N-HC(Q_5)-C(O)-O-$, $H_2N-HC(Q_5)-C(O)-N(H)-$, azidoalkyloxy, cyanoalkyloxy, P.G.-HN-HC($Q_5$)-C(O)-O-, guanidinoalkyloxy, and guanidinoalkylcarboxy, where $Q_5$ is a side chain of any amino acid, P.G. is an amino protecting group.

In some embodiments, at least one, and sometimes two or three, of $R_{1-4}$, $R_6$, $R_7$, $R_{11}$, $R_{12}$, $R_{15}$, $R_{16}$, and $R_{17}$ are independently selected from the group consisting of a substituted or unsubstituted aminoalkyl, a substituted or unsubstituted aminoalkyloxy, a substituted or unsubstituted alkylcarboxyalkyl, a substituted or unsubstituted alkylaminoalkylamino, a substituted or unsubstituted alkylaminoalkylaminoalkylamino, a substituted or unsubstituted aminoalkylcarboxy, a substituted or unsubstituted arylaminoalkyl, a substituted or unsubstituted aminoalkyloxyaminoalkylaminocarbonyl, a substituted or unsubstituted aminoalkylaminocarbonyl, a substituted or unsubstituted aminoalkyl-carboxyamido, a quaternary ammoniumalkylcarboxy, a substituted or unsubstituted di(alkyl)aminoalkyl, $H_2N-HC(Q_5)-C(O)-O-$, $H_2N-HC(Q_5)-C(O)-N(H)-$, azidoalkyloxy, cyanoalkyloxy, P.G.-HN-HC($Q_5$)-C(O)-O-, a substituted or unsubstituted guanidine-alkyloxy, and a substituted or unsubstituted guanidinoalkylcarboxy.

In some embodiments, $R_1$ through $R_4$, $R_6$, $R_7$, $R_{11}$, $R_{12}$, $R_{15}$, and $R_{16}$ are independently selected from the group consisting of hydrogen, hydroxyl, a substituted or unsubstituted ($C_1$-$C_{22}$) alkyl, a substituted or unsubstituted ($C_1$-$C_{22}$) hydroxyalkyl, a substituted or unsubstituted ($C_1$-$C_{22}$) alkyloxy-($C_1$-$C_{22}$) alkyl, a substituted or unsubstituted ($C_1$-$C_{22}$) alkylcarboxy-($C_1$-$C_{22}$) alkyl, a substituted or unsubstituted ($C_1$-$C_{22}$) alkylamino-($C_1$-$C_{22}$) alkyl, a substituted or unsubstituted ($C_1$-$C_{22}$) alkylamino-($C_1$-$C_{22}$) alkylamino, a substituted or unsubstituted ($C_1$-$C_{22}$) alkylamino-($C_1$-$C_{22}$) alkylamino-($C_1$-$C_{22}$) alkylamino, a substituted or unsubstituted ($C_1$-$C_{22}$) aminoalkyl, a substituted or unsubstituted aryl, a substituted or unsubstituted arylamino-($C_1$-$C_{22}$) alkyl, a substituted or unsubstituted ($C_1$-$C_{22}$) haloalkyl, a substituted or unsubstituted $C_2$-$C_6$ alkenyl, a substituted or unsubstituted $C_2$-$C_6$ alkynyl, oxo, a linking group attached to a second steroid, a substituted or unsubstituted ($C_1$-$C_{22}$) aminoalkyloxy, a substituted or unsubstituted ($C_1$-$C_{22}$) aminoalkyloxy-($C_1$-$C_{22}$) alkyl, a substituted or unsubstituted ($C_1$-$C_{22}$) aminoalkylcarboxy, a substituted or unsubstituted ($C_1$-$C_{22}$) aminoalkylaminocarbonyl, a substituted or unsubstituted ($C_1$-$C_{22}$) aminoalkylcarboxamido, a substituted or unsubstituted di($C_1$-$C_{22}$ alkyl)aminoalkyl, $H_2N-HC(Q_5)-C(O)-O-$, $H_2N-HC(Q_5)-C(O)-N(H)-$, a substituted or unsubstituted ($C_1$-$C_{22}$) azidoalkyloxy, a substituted or unsubstituted ($C_1$-$C_{22}$) cyanoalkyloxy, P.G.-HN-HC($Q_5$)-C(O)-O-, a substituted or unsubstituted ($C_1$-$C_{22}$) guanidinoalkyloxy, a substituted or unsubstituted ($C_1$-$C_{22}$) quaternary ammoniumalkylcarboxy, and a substituted or unsubstituted ($C_1$-$C_{22}$) guanidinoalkyl carboxy, where $Q_5$ is a side chain of an amino acid (including a side chain of glycine, i.e., H), and P.G. is an amino protecting group; and $R_5$, $R_8$, $R_9$, $R_{10}$, $R_{13}$, $R_{14}$ and $R_{17}$ are independently deleted when one of rings A, B, C, or D is unsaturated so as to complete the valency of the carbon atom at that site, or $R_5$, $R_8$, $R_9$, $R_{10}$, $R_{13}$, and $R_{14}$ are independently selected from the group consisting of hydrogen, hydroxyl, a substituted or unsubstituted ($C_1$-$C_{22}$) alkyl, a substituted or unsubstituted ($C_1$-$C_{22}$) hydroxyalkyl, a substituted or unsubstituted ($C_1$-$C_{22}$) alkyloxy-($C_1$-$C_{22}$) alkyl, a substituted or unsubstituted ($C_1$-$C_{22}$) aminoalkyl, a substituted or unsubstituted aryl, a substituted or unsubstituted ($C_1$-$C_{22}$) haloalkyl, a substituted or unsubstituted ($C_2$-$C_6$) alkenyl, a substituted or unsubstituted ($C_2$-$C_6$) alkynyl, oxo, a linking group attached to a second steroid, a substituted or unsubstituted ($C_1$-$C_{22}$) aminoalkyloxy, a substituted or unsubstituted ($C_1$-$C_{22}$) aminoalkylcarboxy, a substituted or unsubstituted ($C_1$-$C_{22}$) aminoalkylaminocarbonyl, a substituted or unsubstituted di($C_1$-$C_{22}$ alkyl)aminoalkyl, $H_2N-HC(Q_5)-C(O)-O-$, $H_2N-HC(Q_5)-C(O)-N(H)-$, a substituted or unsubstituted ($C_1$-$C_{22}$) azidoalkyloxy, a substituted or unsubstituted ($C_1$-$C_{22}$) cyanoalkyloxy, P.G.-HN-HC($Q_5$)-C(O)-O-, a substituted or unsubstituted ($C_1$-$C_{22}$) guanidinoalkyloxy, and ($C_1$-$C_{22}$) guanidinoalkylcarboxy, where Q5 is a side chain of any amino acid, and P.G. is an amino protecting group;

provided that at least two or three of $R_{1-4}$, $R_6$, $R_7$, $R_{11}$, $R_{12}$, $R_{15}$, $R_{16}$, $R_{17}$, and $R_{18}$ are independently selected from the group consisting of a substituted or unsubstituted ($C_1$-$C_{22}$) aminoalkyl, a substituted or unsubstituted ($C_1$-$C_{22}$) aminoalkyloxy, a substituted or unsubstituted ($C_1$-$C_{22}$) alkylcarboxy-($C_1$-$C_{22}$) alkyl, a substituted or unsubstituted ($C_1$-$C_{22}$) alkylamino-($C_1$-$C_{22}$) alkylamino, a substituted or unsubstituted ($C_1$-$C_{22}$) alkylamino-($C_1$-$C_{22}$) alkylamino ($C_1$-$C_{22}$) alkylamino, a substituted or unsubstituted ($C_1$-$C_{22}$)

aminoalkylcarboxy, a substituted or unsubstituted arylamino ($C_1$-$C_{22}$) alkyl, a substituted or unsubstituted ($C_1$-$C_{22}$) aminoalkyloxy ($C_1$-$C_{22}$) aminoalkylaminocarbonyl, a substituted or unsubstituted ($C_1$-$C_{22}$) aminoalkylaminocarbonyl, a substituted or unsubstituted ($C_1$-$C_{22}$) aminoalkylcarboxyamido, a substituted or unsubstituted ($C_1$-$C_{22}$) quaternary ammonium alkylcarboxy, a substituted or unsubstituted di($C_1$-$C_{22}$ alkyl)aminoalkyl, $H_2N$—$HC(Q_5)$-$C(O)$—$O$—, $H_2N$—$HC(Q_5)$-$C(O)$—$N(H)$—, a substituted or unsubstituted ($C_1$-$C_{22}$) azidoalkyloxy, a substituted or unsubstituted ($C_1$-$C_{22}$) cyanoalkyloxy, P.G.-HN—$HC(Q_5)$-$C(O)$—$O$—, a substituted or unsubstituted ($C_1$-$C_{22}$) guanidinoalkyloxy, and a substituted or unsubstituted ($C_1$-$C_{22}$) guanidinoalkylcarboxy.

In some embodiments, $R_1$ through $R_4$, $R_6$, $R_7$, $R_{11}$, $R_{12}$, $R_{15}$, and $R_{16}$ are independently selected from the group consisting of hydrogen, hydroxyl, an unsubstituted ($C_1$-$C_{18}$) alkyl, unsubstituted ($C_1$-$C_{18}$) hydroxyalkyl, unsubstituted ($C_1$-$C_{18}$) alkyloxy-($C_1$-$C_{18}$) alkyl, unsubstituted ($C_1$-$C_{18}$) alkylcarboxy-($C_1$-$C_{18}$) alkyl, unsubstituted ($C_1$-$C_{18}$) alkylamino-($C_1$-$C_{18}$)alkyl, unsubstituted ($C_1$-$C_{18}$) alkylamino-($C_1$-$C_{18}$) alkylamino, ($C_1$-$C_{18}$) alkylamino-($C_1$-$C_{18}$) alkylamino-($C_1$-$C_{18}$) alkylamino, an unsubstituted ($C_1$-$C_{18}$) aminoalkyl, an unsubstituted aryl, an unsubstituted arylamino-($C_1$-$C_{18}$) alkyl, oxo, an unsubstituted ($C_1$-$C_{18}$) aminoalkyloxy, an unsubstituted ($C_1$-$C_{18}$) aminoalkyloxy-($C_1$-$C_{18}$) alkyl, an unsubstituted ($C_1$-$C_{18}$) aminoalkylcarboxy, an unsubstituted ($C_1$-$C_{18}$) aminoalkylaminocarbonyl, an unsubstituted ($C_1$-$C_{18}$) aminoalkylcarboxamido, an unsubstituted di($C_1$-$C_{18}$ alkyl)aminoalkyl, unsubstituted ($C_1$-$C_{18}$) guanidinoalkyloxy, unsubstituted ($C_1$-$C_{18}$) quaternary ammonium alkylcarboxy, and unsubstituted ($C_1$-$C_{18}$) guanidinoalkyl carboxy; and $R_5$, $R_8$, $R_9$, $R_{10}$, $R_{13}$, $R_{14}$ and $R_{17}$ are independently deleted when one of rings A, B, C, or D is unsaturated so as to complete the valency of the carbon atom at that site, or $R_5$, $R_8$, $R_9$, $R_{10}$, $R_{13}$, and $R_{14}$ are independently selected from the group consisting of hydrogen, hydroxyl, an unsubstituted ($C_1$-$C_{18}$) alkyl, unsubstituted ($C_1$-$C_{18}$) hydroxyalkyl, unsubstituted ($C_1$-$C_{18}$) alkyloxy-($C_1$-$C_{18}$) alkyl, unsubstituted ($C_1$-$C_{18}$) alkylcarboxy-($C_1$-$C_{18}$) alkyl, unsubstituted ($C_1$-$C_{18}$) alkylamino-($C_1$-$C_{18}$)alkyl, ($C_1$-$C_{18}$) alkylamino-($C_1$-$C_{18}$) alkylamino, unsubstituted ($C_1$-$C_{18}$) alkylamino-($C_1$-$C_{18}$) alkylamino-($C_1$-$C_{18}$) alkylamino, an unsubstituted ($C_1$-$C_{18}$) aminoalkyl, an unsubstituted aryl, an unsubstituted arylamino-($C_1$-$C_{18}$) alkyl, oxo, an unsubstituted ($C_1$-$C_{18}$) aminoalkyloxy, an unsubstituted ($C_1$-$C_{18}$) aminoalkyloxy-($C_1$-$C_{18}$) alkyl, an unsubstituted ($C_1$-$C_{18}$) aminoalkylcarboxy, an unsubstituted ($C_1$-$C_{18}$) aminoalkylaminocarbonyl, an unsubstituted ($C_1$-$C_{18}$) aminoalkylcarboxamido, an unsubstituted di($C_1$-$C_{18}$ alkyl)aminoalkyl, unsubstituted ($C_1$-$C_{18}$) guanidinoalkyloxy, unsubstituted ($C_1$-$C_{18}$) quaternary ammonium alkylcarboxy, and unsubstituted ($C_1$-$C_{18}$) guanidinoalkyl carboxy, provided that at least one of $R_{1-4}$, $R_6$, $R_7$, $R_{11}$, $R_{12}$, $R_{15}$, $R_{16}$, and $R_{17}$ are independently selected from the group consisting of hydrogen, hydroxyl, an unsubstituted ($C_1$-$C_{18}$) alkyl, unsubstituted ($C_1$-$C_{18}$) hydroxyalkyl, unsubstituted ($C_1$-$C_{18}$) alkyloxy-($C_1$-$C_{18}$) alkyl, unsubstituted ($C_1$-$C_{18}$ alkylcarboxy-($C_1$-$C_{18}$) alkyl, unsubstituted ($C_1$-$C_{18}$) alkylamino-($C_1$-$C_{18}$) alkyl, unsubstituted ($C_1$-$C_{18}$) alkylamino-($C_1$-$C_{18}$) alkylamino, unsubstituted ($C_1$-$C_{18}$ alkylamino-($C_1$-$C_{18}$) alkylamino-($C_1$-$C_{18}$) alkylamino, an unsubstituted ($C_1$-$C_{18}$) aminoalkyl, an unsubstituted aryl, an unsubstituted arylamino-($C_1$-$C_{18}$) alkyl, oxo, an unsubstituted ($C_1$-$C_{18}$) aminoalkyloxy, an unsubstituted ($C_1$-$C_{18}$) aminoalkyloxy-($C_1$-$C_{18}$) alkyl, an unsubstituted ($C_1$-$C_{18}$) aminoalkylcarboxy, an unsubstituted ($C_1$-$C_{18}$) aminoalkylaminocarbonyl, an unsubstituted ($C_1$-$C_{18}$) aminoalkylcarboxamido, an unsubstituted di($C_1$-$C_{18}$ alkyl)aminoalkyl, unsubstituted ($C_1$-$C_{18}$) guanidinoalkyloxy, unsubstituted ($C_1$-$C_{18}$) quaternary ammonium alkylcarboxy, and unsubstituted ($C_1$-$C_{18}$) guanidinoalkyl carboxy.

In some embodiments, $R_1$, $R_2$, $R_4$, $R_5$, $R_6$, $R_8$, $R_9$, $R_{10}$, $R_{11}$, $R_{13}$, $R_{14}$, $R_{15}$, $R_{16}$, and $R_{17}$ are independently selected from the group consisting of hydrogen and unsubstituted ($C_1$-$C_6$) alkyl.

In some embodiments, $R_1$, $R_2$, $R_4$, $R_5$, $R_6$, $R_8$, $R_{10}$, $R_{11}$, $R_{14}$, $R_{16}$, and $R_{17}$ are each hydrogen; and $R_9$ and $R_{13}$ are each methyl.

In some embodiments, one or more of rings A, B, C, and D are heterocyclic.

In some embodiments, rings A, B, C, and D are non-heterocyclic.

In some embodiments, the CSA compound is a compound of Formula (III), or salt thereof, having a steroidal backbone, and wherein at least $R_{18}$ of the steroidal backbone includes a heterocyclic ring spaced apart from the steroidal backbone by at least 4 atoms:

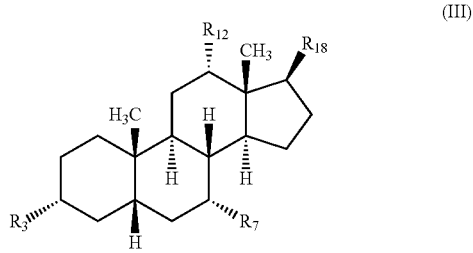

(III)

wherein,
at least $R_{18}$ has the following structure:

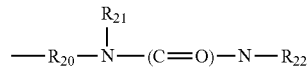

$R_{20}$ is omitted or is an alkyl, alkenyl, alkynyl, or aryl;

$R_{21}$ is selected from the group consisting of hydrogen, $C_1$-$C_{24}$ alkyl, $C_2$-$C_{24}$ alkenyl, $C_2$-$C_{24}$ alkynyl, $C_6$ or $C_{10}$ aryl, 5 to 10 membered heteroaryl, 5 to 10 membered heterocyclyl, $C_7$-$C_{13}$ aralkyl, (5 to 10 membered heteroaryl)-$C_1$-$C_6$ alkyl, $C_3$-$C_{10}$ carbocyclyl, $C_4$-$C_{10}$ (carbocyclyl)alkyl, (5 to 10 membered heterocyclyl)-$C_1$-$C_6$ alkyl, amido, and a suitable amine protecting group; and $R_{22}$ is a 5 to 13 member, 8 to 12 member, or 9 to 10 member heterocyclyl joined to the rest of the compound by a linkage selected from the group consisting of alkyl, -[alkoxy]$_n$-, -[alkoxy]$_n$-alkyl, alkylcarboxamido-alkyl, alkylcarboxamido-[alkoxy]$_n$, alkylcarboxamido-[alkoxy]$_n$-alkyl, alkylcarboxyalkyl, alkylaminoalkyl, aryl, arylaminoalkyl, alkenyl, and alkynyl, where n is 1 to 10; and wherein each of $R_{20}$, $R_{21}$, and $R_{22}$ may be optionally substituted.

In some embodiments, $R_3$, $R_7$, and $R_{12}$ are independently selected from the group consisting of hydrogen, an unsubstituted ($C_1$-$C_{22}$) alkyl, unsubstituted ($C_1$-$C_{22}$) hydroxyalkyl, unsubstituted ($C_1$-$C_{22}$) alkyloxy-($C_1$-$C_{22}$) alkyl, unsubstituted ($C_1$-$C_{22}$) alkylcarboxy-($C_1$-$C_{22}$) alkyl, unsubstituted ($C_1$-$C_{22}$) alkylamino-($C_1$-$C_{22}$)alkyl, unsubstituted ($C_1$-$C_{22}$) alkylamino-($C_1$-$C_{22}$) alkylamino, unsubstituted ($C_1$-$C_{22}$) alkylamino-($C_1$-$C_{22}$) alkylamino-($C_1$-$C_{22}$) alkylamino, an unsubstituted ($C_1$-$C_{22}$) aminoalkyl, an unsubstituted arylamino-($C_1$-$C_{22}$) alkyl, an unsubstituted ($C_1$-$C_{22}$) aminoalkyloxy, an unsubstituted ($C_1$-$C_{22}$) aminoalkyloxy-($C_1$-$C_2$) alkyl, an unsubstituted ($C_1$-$C_{22}$) aminoalkylcarboxy, an unsubstituted ($C_1$-$C_{22}$) aminoalkylaminocarbonyl, an unsubstituted ($C_1$-$C_{22}$) aminoalkylcarboxamido, an unsubstituted di($C_1$-$C_{22}$ alkyl)aminoalkyl, unsubstituted ($C_1$-$C_{22}$) guanidinoalkyloxy, unsubstituted ($C_1$-$C_{22}$) quaternary ammonium alkylcarboxy, and unsubstituted ($C_1$-$C_{22}$) guanidinoalkyl carboxy.

In some embodiments, $R_3$, $R_7$, and $R_{12}$ are independently selected from the group consisting of hydrogen, an unsubstituted ($C_1$-$C_6$) alkyl, unsubstituted ($C_1$-$C_6$) hydroxyalkyl, unsubstituted ($C_1$-$C_{16}$) alkyloxy-($C_1$-$C_5$) alkyl, unsubstituted ($C_1$-$C_{16}$) alkylcarboxy-($C_1$-$C_5$) alkyl, unsubstituted ($C_1$-$C_{16}$) alkylamino-($C_1$-$C_5$)alkyl, unsubstituted ($C_1$-$C_{16}$) alkylamino-($C_1$-$C_5$) alkylamino, unsubstituted ($C_1$-$C_{16}$) alkylamino-($C_1$-$C_{16}$) alkylamino-($C_1$-$C_5$) alkylamino, an unsubstituted ($C_1$-$C_{16}$) aminoalkyl, an unsubstituted arylamino-($C_1$-$C_5$) alkyl, an unsubstituted ($C_1$-$C_5$) aminoalkyloxy, an unsubstituted ($C_1$-$C_{16}$) aminoalkyloxy-($C_1$-$C_5$) alkyl, an unsubstituted ($C_1$-$C_5$) aminoalkylcarboxy, an unsubstituted ($C_1$-$C_5$) aminoalkylaminocarbonyl, an unsubstituted ($C_1$-$C_5$) aminoalkylcarboxamido, an unsubstituted di($C_1$-$C_5$ alkyl)amino-($C_1$-$C_5$) alkyl, unsubstituted ($C_1$-$C_5$) guanidinoalkyloxy, unsubstituted ($C_1$-$C_{16}$) quaternary ammonium alkylcarboxy, and unsubstituted ($C_1$-$C_{16}$) guanidinoalkylcarboxy.

In some embodiments, $R_3$, $R_7$, and $R_{12}$ are independently selected from the group consisting of aminoalkyloxy; aminoalkylcarboxy; alkylaminoalkyl; alkoxycarbonylalkyl; alkylcarbonylalkyl; di(alkyl)aminoalkyl; alkylcarboxyalkyl; and hydroxyalkyl.

In some embodiments, $R_3$, $R_7$, and $R_{12}$ are independently selected from the group consisting of aminoalkyloxy and aminoalkylcarboxy.

In some embodiments, $R_3$, $R_7$, and $R_{12}$ are the same. In some embodiments, $R_3$, $R_7$, and $R_{12}$ are aminoalkyloxy. In some embodiments, $R_3$, $R_7$, and $R_{12}$ are aminoalkylcarboxy.

In some embodiments, $R_3$, $R_7$, and $R_{12}$ are independently selected from the group consisting of amino-$C_3$-alkyloxy; amino-$C_3$-alkyl-carboxy; $C_8$-alkylamino-$C_5$-alkyl; $C_8$-alkoxy-carbonyl-$C_4$-alkyl; $C_8$-alkyl-carbonyl-$C_4$-alkyl; di-($C_5$-alkyl)amino-$C_5$-alkyl; $C_{13}$-alkylamino-$C_5$-alkyl; $C_6$-alkoxy-carbonyl-$C_4$-alkyl; $C_6$-alkyl-carboxy-$C_4$-alkyl; and $C_{16}$-alkylamino-$C_5$-alkyl.

Non-limiting examples of CSA compounds having heterocyclic ring functionality spaced at least 4 atoms apart from the steroidal backbone include CSA-150, CSA-151, CSA-153, and salts thereof. Another aspect of these CSA compounds, though not necessarily critical to how they function, is that they include urea functionality at the C-24 carbon position located on $R_{18}$ to which the heterocyclic ring is attached. Another aspect of these CSA compounds, though not necessarily critical to how they function, is that they include urea functionality interconnecting the heterocyclic ring and a linking group extending from the urea functionality at the C-24 carbon.

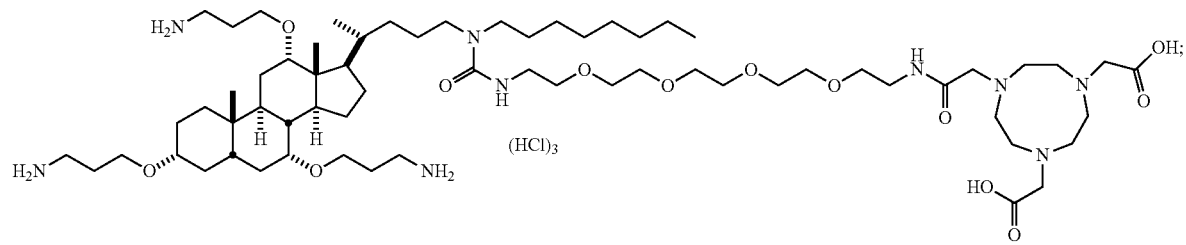

(CSA-150)

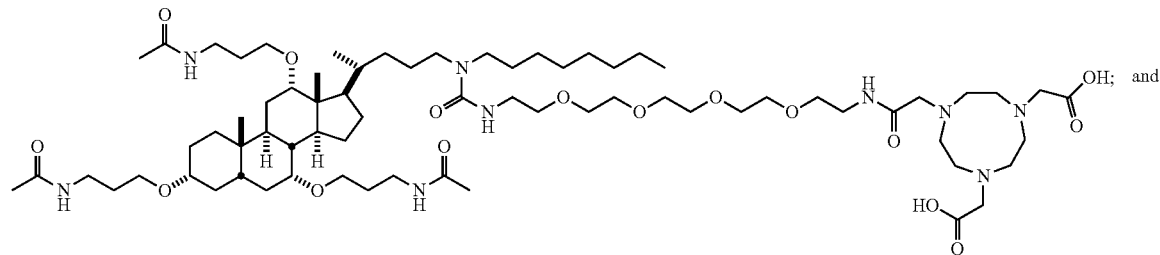

(CSA-151) and (CSA-153)

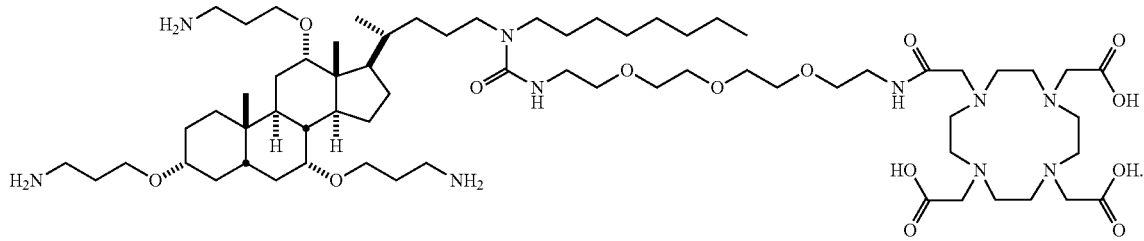

Detectable Labels

Detectable labels include labels suitable for diagnosis, detection, screening or imaging. A detectable label can be included with or within the structure of the CSA. As the structure of CSAs includes carbon, hydrogen, nitrogen, oxygen, sulfur, etc., radioisotopes of any of carbon, hydrogen, nitrogen, oxygen, sulfur, etc., can be included or within a CSA structure such that the CSA is detectably labelled.

A detectable label can also be covalently linked or conjugated to the CSA or may complex with the CSA or a portion of the CSA. Non-limiting exemplary detectable labels include a radioactive material, such as a radioisotope, a metal or a metal oxide. In particular embodiments, a radioisotope can be one or more of: C, N, O, H, S, Cu, Fe, Ga, Ti, Sr, Y, Tc, In, Pm, Gd, Sm, Ho, Lu, Re, At, Bi or Ac. In additional embodiments, radioisotope can be one or more of: $^{3}$H, $^{10}$B, $^{18}$F, $^{11}$C, $^{14}$C, $^{13}$N, $^{18}$O, $^{15}$O, $^{32}$P, $^{35}$Cl, $^{45}$Ti, $^{46}$Sc, $^{51}$Cr, $^{52}$Fe, $^{59}$Fe, $^{57}$Co, $^{60}$Cu, $^{61}$Cu, $^{62}$Cu, $^{64}$Cu, $^{67}$Cu, $^{67}$Ga, $^{68}$Ga, $^{72}$As, $^{76}$Br, $^{77}$Br, $^{81m}$Kr, $^{82}$Rb, $^{85}$Sr, $^{89}$Sr, $^{86}$Y, $^{90}$Y, $^{95}$Nb, $^{94m}$Tc, $^{99m}$Tc, $^{97}$Ru, $^{103}$Ru, $^{105}$Rh, $^{109}$Cd, $^{111}$In, $^{113}$Sn, $^{113}$In, $^{114}$In, $^{140}$La, $^{141}$Ce, $^{149}$Pm, $^{153}$Gd, $^{157}$Gd, $^{153}$Sm, $^{161}$Tb, $^{166}$Dy, $^{166}$Ho, $^{169}$Er, $^{169}$Y, $^{175}$Yb, $^{177}$Lu, $^{186}$Re, $^{188}$Re, $^{201}$Tl, $^{203}$Pb, $^{211}$At, $^{212}$Bi, or $^{225}$Ac. In more particular embodiments, a radionuclide includes technetium and rhenium isotopes, more specifically, for example, technetium-99m, rhenium-186 and rhenium-188.

Radionuclides include, but are not limited to, isotopes emitting alpha, beta or gamma radiation. In diagnostic, screening, detection and imaging methods. Non-limiting examples of beta emitters include cesium-137, cobalt-60, radium-226, and technetium-99m.

CSAs typically include several basic sites (oxygen, sulfur, and nitrogen lone pairs) which are suitable for binding cationic radionuclides and metals. This allows easy and optionally reversible complexation of the CSA with the radionuclide or metal. Thus, detectably labeled CSAs can include cationic radionuclides and cationic metals.

Additionally, as a non-limiting example, particular embodiments of CSAs may include one or more chelator moieties. For example, some embodiments may include a macrocyclic chelator and may complex with a wide variety of metal ions, such as bi- and trivalent metal ions. For example, in some embodiments of CSAs of the present disclosure, a CSA may include a 1,4,7-triazacyclononane-N,N',N"-triacetic acid (NOTA) moiety or derivative thereof.

Additional non-limiting exemplary detectable labels include a metal or metal oxide. In particular embodiments, a metal or metal oxide is one or more of: gold, silver, copper, boron, manganese, gadolinium, iron, chromium, barium, europium, erbium, praseodynium, indium, or technetium. In additional embodiments, a metal oxide includes one or more of: Gd(III), Mn(II), Cr(II), Cr(III), Cu(II), Fe(III), Pr(III), Nd(III) Sm(III), Tb(M), Yb(III) Dy(II), Ho Eu(II), Eu(III), or Er(III). Metals and oxides include crystals.

A label can also be a contrast agent (e.g., gadolinium; manganese; barium sulfate; an iodinated or noniodinated agent; an ionic agent or nonionic agent); a magnetic agent or a paramagnetic agent (e.g., gadolinium, iron-oxide chelate); nanoparticles; an enzyme (horseradish peroxidase, alkaline phosphatase, beta.-galactosidase, or acetylcholinesterase); a prosthetic group (e.g., streptavidin/biotin and avidinfbiotin); a fluorescent material (e.g., umbelliferone, fluorescein, fluorescein isothiocyanate, rhodamine, dichlorotriazinylamine fluorescein, dansyl chloride or phycoerythrin); or a luminescent material (e.g., luminol). A label can also be a bioluminescent material (e.g., luciferase, luciferin, aequorin); or any other imaging agent that can be employed for detection, screening, diagnostic, or imaging (e.g., for CT, fluoroscopy, SPECT imaging, optical imaging, PET, MRI, gamma imaging).

Detectable Conditions

The term "infection" means an initial or primary (acute) or a chronic infection. An infection may be "infectious" in the sense that other sites in the infected host subject, or contagious to other subjects (cross-infection), or may be latent. An initial/primary (acute) infection can cause mild, moderate or severe pathogenesis or symptoms, or be asymptomatic. A primary/initial infection may or may not be self-limiting, and can become progressively worse, or become latent. A "latent" infection in a host subject is a state in which the infection (e.g., virus) evades immune clearance and remains in the host subject, which infection can be chronic, even lifelong. In the latent state illness or symptoms may not be present or may be mild. Reactivation of an infection means activation in the host subject following a period of latency. Reactivation is associated with increased replication and proliferation in a subject. Symptoms and pathologies associated with or caused by reactivation may also increase.

Specific non-limiting examples of infections include chronic, acute or latent bacterial (gram negative and gram positive and non-gram staining) viral, parasite and fungal infections. Infections can be either pathogenic or non-pathogenic infections (e.g., pathogenic or non-pathogenic bacterial, viral, parasite and fungal infections).

Specific non-limiting examples of gram negative bacterial infections include: *Bordetella, Bordetella pertussis, Borrelia, Borrelia burgdorferi, Brucella, Brucella abortus, Brucella canis, Brucella melitensis, Brucella suis, Campylobacter, Campylobacter jejuni, Escherichia, Escherichia coli, Francisella, Francisella tularensis, Haemophilus, Haemophilus influenza, Helicobacter, Helicobacter pylori, Legionella, Legionella pneumophila, Leptospira, Leptospira interrogans, Neisseria, Neisseria gonorrhoeae, Neisseria meningitides, Pseudomonas, Pseudomonas aeruginosa,*

*Rickettsia, Rickettsia rickettsii, Salmonella, Salmonella typhi, Salmonella typhimurium, Shigella, Shigella sonnei; Treponema, Treponema pallidum; Vibrio, Vibrio cholerae; Yersinia,* and *Yersinia pestis.*

Specific non-limiting examples of gram positive bacterial infections include: *Clostridium, Clostridium botulinum, Clostridium difficile, Clostridium perfringens, Clostridium tetani, Corynebacterium, Corynebacterium diphtheria, Enterococcus, Enterococcus faecalis, Enterococcus faecum, Listeria, Listeria monocytogenes, Staphylococcus, Staphylococcus aureus, Staphylococcus epidermidis, Staphylococcus saprophyticus, Streptococcus, Streptococcus agalactiae, Streptococcus pneumonia,* and *Streptococcus pyogenes.*

Specific non-limiting examples of non-gram staining bacteria include: *Chlamydia, Chlamydia pneumoniae, Chlamydia psittaci, Chlamydia trachomatis, Mycobacterium, Mycobacterium leprae, Mycobacterium tuberculosis, Mycoplasma,* and *Mycoplasma pneumoniae.*

Specific non-limiting examples of viral infections include poxvirus, herpesvirus, hepatitis virus, immunodeficiency virus, flavivirus, papilloma virus (PV), polyoma virus, rhabdovirus, a myxovirus, an arenavirus, a coronavirus, adenovirus, reovirus, picornavirus, togavirus, bunyavirus, parvovirus or retrovirus.

Poxviruses include a vaccinia virus, Molluscum contagiosum, variola major smallpox virus, variola minor smallpox virus, cow pox, camel pox, sheep pox, and monkey pox. Herpesviruses include alpha-herpesvirus, beta-herpesvirus, gamma-herpesvirus, Epstein Bar Virus (EBV), Cytomegalovirus (CMV), varicella zoster virus (VZV/1-1HV-3), and human herpes simplex virus-1 (HSV-1), herpes simplex virus-2 (HSV-2) and varicella zoster virus (VZV/HHV-3). Particular non-limiting examples of beta- and gamma-herpesvirus include cytomegalovirus (CMV), Epstein-Barr virus (EBV), human herpes virus-6, -7 and -8 (HHV-6, HHV-7, or HHV-8/Kaposi's sarcoma herpesvirus/KSHV). Hepatitis viruses include hepatitis A, B, C, D, E and G. Immunodeficiency viruses include human immunodeficiency virus (HIV), such as HIV-1, HIV-2 and HIV-3. Flaviviruses include Hepatitis C virus, Yellow Fever virus, Dengue virus, and Japanese Encephalitis and West Nile viruses. Papilloma viruses include human papilloma virus (HPV), such as HPV strain 1, 6, 11, 16, 18, 30, 31, 42, 43, 44, 45, 51, 52, and 54. Polyoma viruses include BK virus (BKV) and JC virus (JCV). Rhabdoviruses include rabies virus and vesiculovirus. Myxoviruses include paramyxovirus (e.g., measles, mumps, pneumovirus and respiratory syncytial virus (RSV) and orthomyxovirus (e.g., influenza virus, such as influenza A, influenza B and influenza C). Arenaviruses include lymphocytic choriomeningitis virus (LCMV), Junin virus, Lassa virus, Guanarito virus, Sabia virus and Machupo virus. Coronaviruses include viruses that cause a common cold or severe acute respiratory syndrome (SARS). Adenoviruses include viral infections of the bronchii, lung, stomach, intestine (gastroenteritis), eye (conjunctivitis), bladder (cystitis) and skin. Reoviruses include a rotavirus, cypovirus and orbivirus. Picornaviruses include rhinovirus (e.g., causing a common cold), apthovirus, hepatovirus, enterovirus, coxsackie B virus and cardiovirus. Togaviruses include alphavirus, sindbus virus, and rubellavirus. Bunyaviruses incltide hantavirus, phlebovirus and nairovirus. Retroviruses include alpha, beta, delta, gamma, epsilon, lentivirus, spumavirus and human T-cell leukemia virus, such as human T-cell leukemia virus 1 and 2 (HTLV-1 and HTLV-2). Lentiviruses include immunodeficiency virus, such as bovine, porcine, equine, canine, feline and primate virus.

Specific non-limiting examples of parasites include a protozoa or nematode. Exemplary protozoa include a *Toxoplasma gondii, Leishmania, Plasmodium,* or *Trypanosoma cruzi*. Exemplary nematodes include a *Schistosoma mansoni,* or aHeligmosomoides polygyrus. Exemplary fungus includes *Candida albicans*.

Neoplasias, tumors and cancers that can be diagnosed, detected, screened for, or imaged include sarcoma, carcinoma, adenocarcinoma, melanoma, myeloma, blastoma, glioma, lymphoma or leukemia. Exemplary cancers include, for example, carcinoma, sarcoma, adenocarcinoma, melanoma, neural (blastoma, glioma), mesothelioma and reticuloendothelial, lymphatic or haematopoietic neoplastic disorders (e.g., myeloma, lymphoma or leukemia).

Neoplasia, tumors and cancers include benign, malignant, metastatic and non-metastatic types, and include any stage (I, II, III, IV or V) or grade (G1, G2, G3, etc.) of neoplasia, tumor, or cancer, or a neoplasia, tumor, cancer or metastasis that is progressing, worsening, stabilized or in remission.

An infection or hyperproliferative disease may arise from any cause or may affect any part of the body of a subject. Exemplary parts (e.g., organ, tissue) affected include skin, dermis, breast, lung, nasopharynx, nose or sinuses, thyroid, head, neck, brain, spine, adrenal gland, thyroid, lymph, blood, gastrointestinal (mouth, esophagug, stomach, duodenum, ileum, jejunum (small intestine), colon, rectum), genito-urinary tract (uterus, ovary, endometrium, cervix, bladder, testicle, penis, urinary tract, prostate), kidney, pancreas, adrenal gland, liver, bone, bone marrow, heart, muscle, and the hematopoetic system. Thus, a method of the disclosure may be performed to diagnose, detect, screen, or image an infection in the whole body of a subject, a particular region or general area, a specific organ or tissue, or a local portion of a region, organ or tissue.

Detection and/or Diagnosis

Methods of the disclosure include detecting the type, kind, presence or absence, location or extent of an infection. Such methods can be used to alternatively or additionally provide information on severity or progression of infection; prognosis of infection; and/or therapy or treatment of infection based upon detecting, diagnosing, screening or imaging.

As used herein, a "sufficient amount" or "effective amount" or an "amount sufficient" or an "amount effective" refers to an amount that is sufficient to detect an infection. Typically, the amount is less than an amount that leads to substantial lysis or killing of the target infection. Thus, an amount sufficient or effective is that amount to allow detection, diagnosis, screening or imaging, without substantial cell or infection killing such that an infection is no longer detected, diagnosed, or imaged. Further, the amount of labeled CSA may vary with the particular label used and the method of detection in order to achieve a desired image.

Methods of detection, diagnostics or screening, such as in vitro, ex vivo, and vivo imaging methods, permit the detection of a labeled CSA. Such methods of CSA detection include magnetic resonance spectroscopy (MRS), magnetic resonance imaging (MRI), positron-emission tomography (PET), gamma-scintigraphy, computed tomography (CT), Computed Axial Tomography (CAT), or single photon emission tomography (SPECT).

Methods also include detecting an infection, or diagnosing a subject having or at risk of having an infection (in vitro, ex vivo and in vivo). Such methods include contacting a detectably labeled CSA to a biological sample from a subject under conditions whereby the labeled CSA can bind to an infection in the sample, and detecting the labeled CSA in the sample to ascertain the presence or absence of an infection in the sample, thereby of detecting an infection or diagnosing the subject as having or not having an infection.

Biological samples include any sample capable of having a biological material. Specific non-limiting examples include mucus, saliva, feces, blood, serum, plasma, cerebrospinal fluid, urine, or placenta. Biological samples also include biopsies, for example, of skin, dermis, breast, lung, nasopharynx, nose or sinuses, thyroid, head, neck, adrenal gland, thyroid, lymph, gastrointestinal tract, genito-urinary tract, kidney, pancreas, adrenal gland, liver, bone, bone marrow, heart, muscle, or a sample of the hematopoetic system.

For in vitro, ex vivo, and in vivo diagnosing, detecting, screening or imaging, the type of detection instrument available can depend upon a given label or conjugate. As an example, a radioisotope or paramagnetic isotope is suitable for in vivo detection, diagnosis, screening or imaging. The type of label, such as a radionuclide or metal, will guide the selection of the instrument used. For instance, decay parameters of a chosen alpha, beta, or gamma radionuclide chosen can be detectable or measured by the selected instrument.

In various embodiments a label or conjugate, such as a radionuclide or metal or metal oxide can be bound to a CSA, either directly or indirectly, using an intermediary functional group. Intermediary functional groups which are often used to bind radioisotopes which exist as, for example, metallic ions (e.g. cations) that bind to groups on the CSAs. Examples include agents that react with free or semi-free amines, oxygen, sulfur, hydroxy or carboxy groups. Such functional groups therefore include mono and bifunctional crosslinkers, such as DSS, BS3 (Sulfo-DSS), DSG. Non-limiting examples include diethylenetriaminepentaacetic acid (DTPA) and ethylene diaminetetracetic acid (EDTA). Additional functional groups include carbon esideus, or one or more of a succinly groups, such as disulfosuccinimidyl tartarate, disuccinimidyl glutarate and disuccinimidyl suberate.

A "subject" refers to an animal, typically mammalian animals, such as but not limited to non-human primates (apes, gibbons, gorillas, chimpanzees, orangutans, macaques), domestic animals (dogs and cats), farm animals (chickens, ducks, horses, cows, goats, sheep, pigs), experimental animal (mouse, rat, rabbit, guinea pig) and humans. Subjects include animal models, for example, a mouse model of an infection. Subjects include naturally occurring or non-naturally occurring mutated or non-human genetically engineered (e.g., transgenic or knockout) animals. Subjects further include animals having or at risk of having an infection. Subjects can be any age. For example, a subject (e.g., human) can be a newborn, infant, toddler, child, teenager, or adult, e.g., 50 years or older.

Subjects include those in need of a method of the disclosure, e.g., in need of diagnosis, detection, screening or imaging. A subject is considered to be in need of a method of the disclosure where a method is likely to provide information concerning the presence or absence of, the extent or severity of, the status or prognosis of, or possible treatment or therapy of, an infection.

Subjects appropriate for treatment therefore include those having or at risk of having an infection. At risk subjects include subjects that have been exposed to an infection or infectious agent. A subject may therefore be symptomatic or asymptomatic for an infection. Candidate subjects therefore include subjects that have been exposed to or contacted with an infection, or that are at risk of exposure to or contact with an infection, regardless of the type, timing or extent of exposure or contact. The disclosure methods are therefore applicable to a subject who is at risk of an infection, but has not yet been diagnosed for an infection. Prophylactic methods are therefore included.

Pharmaceutical Compositions

Compounds of the disclosure, including CSAs, can be incorporated into pharmaceutical compositions or formulations. Such pharmaceutical compositions/formulations are useful for administration to a subject, in vivo or ex vivo.

Pharmaceutical compositions and formulations include carriers or excipients for administration to a subject. As used herein the terms "pharmaceutically acceptable" and "physiologically acceptable" mean a biologically compatible formulation, gaseous, liquid or solid, or mixture thereof, which is suitable for one or more routes of administration, in vivo delivery or contact. A formulation is compatible in that it does not destroy activity of an active ingredient therein (e.g., a CSA), or induce adverse side effects that far outweigh any prophylactic or therapeutic effect or benefit.

Such formulations include solvents (aqueous or non-aqueous), solutions (aqueous or non-aqueous), emulsions (e.g., oil-in-water or water-in-oil), suspensions, syrups, elixirs, dispersion and suspension media, coatings, isotonic and absorption promoting or delaying agents, compatible with pharmaceutical administration or in vivo contact or delivery. Aqueous and non-aqueous solvents, solutions and suspensions may include suspending agents and thickening agents. Such pharmaceutically acceptable carriers include tablets (coated or uncoated), capsules (hard or soft), microbeads, powder, granules and crystals. Supplementary active compounds (e.g., preservatives, antibacterial, antiviral and antifungal agents) can also be incorporated into the compositions.

The formulations may, for convenience, be prepared or provided as a unit dosage form. Preparation techniques include bringing into association the active ingredient (e.g., CSA) and a pharmaceutical carrier(s) or excipient(s). In general, formulations are prepared by uniformly and intimately associating the active ingredient with liquid carriers or finely divided solid carriers or both, and then, if necessary, shaping the product. For example, a tablet may be made by compression or molding. Compressed tablets may be prepared by compressing, in a suitable machine, an active ingredient (e.g., a CSA) in a free-flowing form such as a powder or granules, optionally mixed with a binder, lubricant, inert diluent, preservative, surface-active or dispersing agent. Molded tablets may be produced by molding, in a suitable apparatus, a mixture of powdered compound (e.g., CSA) moistened with an inert liquid diluent. The tablets may optionally be coated or scored and may be formulated so as to provide a slow or controlled release of the active ingredient therein.

Pharmaceutical compositions can optionally be formulated to be compatible with a particular route of administration. Exemplary routes of administration include administration to a biological fluid or tissue, mucosal cell or tissue (e.g., mouth, buccal cavity, labia, nasopharynx, esophagus, trachea, lung, stomach, small intestine, vagina, rectum, or colon), neural cell or tissue (e.g., ganglia, motor or sensory neurons) or epithelial cell or tissue (e.g., nose, fingers, ears, cornea, conjunctiva, skin or dermis). Thus, pharmaceutical compositions include carriers (excipients, diluents, vehicles or filling agents) suitable for administration to any cell, tissue or organ, in vivo, ex vivo (e.g., tissue or organ transplant) or in vitro, by various routes and delivery, locally, regionally or systemically.

Exemplary routes of administration for contact or in vivo delivery which a compound of the disclosure (e.g., CSA) can optionally be formulated include inhalation, respiration, intubation, intrapulmonary instillation, oral (buccal, sublingual, mucosal), intrapulmonary, rectal, vaginal, intrauterine, intradermal, topical, dermal, parenteral (e.g., subcutaneous, intramuscular, intravenous, intradermal, intraocular, intratracheal and epidural), intranasal, intrathecal, intraarticular, intracavity, transdermal, iontophoretic, ophthalmic, optical (e.g., corneal), intraglandular, intraorgan, intralymphatic.

Formulations suitable for parenteral administration include aqueous and non-aqueous solutions, suspensions or emulsions of the compound, which may include suspending agents and thickening agents, which preparations are typically sterile and can be isotonic with the blood of the intended recipient. Non-limiting illustrative examples of aqueous carriers include water, saline (sodium chloride solution), dextrose (e.g., Ringer's dextrose), lactated Ringer's, fructose, ethanol, animal, vegetable or synthetic oils. Examples of non-aqueous solvents are propylene glycol, polyethylene glycol, vegetable oils such as olive oil, and injectable organic esters such as ethyl oleate. Intravenous vehicles include fluid and nutrient replenishers, electrolyte replenishers (such as those based on Ringer's dextrose). The formulations may be presented in unit-dose or multi-dose kits, for example, ampules and vials, and may be stored in a freeze-dried (lyophilized) condition requiring addition of a sterile liquid carrier, for example, water for injections, prior to use.

For transmucosal or transdermal administration (e.g., topical contact), penetrants can be included in the pharmaceutical composition. Penetrants are known in the art, and include, for example, for transmucosal administration, detergents, bile salts, and fusidic acid derivatives. For transdermal administration, the active ingredient can be formulated into aerosols, sprays, ointments, salves, gels, pastes, lotions, oils or creams as generally known in the art.

For topical administration, for example, to skin, pharmaceutical compositions typically include ointments, creams, lotions, pastes, gels, sprays, aerosols or oils. Carriers which may be used include Vaseline, lanolin, polyethylene glycols, alcohols, transdermal enhancers, and combinations thereof.

For oral administration, aceutical compositions include capsules, cachets, lozenges, tablets or troches, as powder or granules. Oral administration formulations also include a solution or a suspension (e.g., aqueous liquid or a non-aqueous liquid; or as an oil-in-water liquid emulsion or a water-in-oil emulsion).

For airway or nasal administration, pharmaceutical compositions can be formulated in a dry powder for delivery, such as a fine or a coarse powder having a particle size, for example, in the range of 20 to 500 microns which is administered in the manner by inhalation through the airways or nasal passage. Depending on delivery device efficiency, effective dry powder dosage levels typically fall in the range of about 10 to about 100 mg. Appropriate formulations, wherein the carrier is a liquid, for administration, as for example, a nasal spray or as nasal drops, include aqueous or oily solutions of the active ingredient. Dry-powder inhalers (DPI) can be used to deliver the compounds (CSAs), either alone or in combination with a pharmaceutically acceptable carrier.

For airway or nasal administration, aerosol and spray delivery systems and devices, also referred to as "aerosol generators" and "spray generators," such as metered dose inhalers (MDI), nebulizers (ultrasonic, electronic and other nebulizers), nasal sprayers and dry powder inhalers can be used. MDIs typically include an actuator, a metering valve, and a container that holds a suspension or solution, propellant, and surfactant (e.g., oleic acid, sorbitan trioleate, lecithin). Activation of the actuator causes a predetermined amount to be dispensed from the container in the form of an aerosol, which is inhaled by the subject.

For rectal administration, pharmaceutical compositions can be included as a suppository with a suitable base comprising, for example, cocoa butter or a salicylate. For vaginal administration, pharmaceutical compositions can be included as pessaries, tampons, creams, gels, pastes, foams or spray formulations containing in addition to the active ingredient (e.g., CSA) a carrier, examples of appropriate carriers which are known in the art.

Pharmaceutical formulations and delivery systems appropriate for the compositions and methods of the disclosure are known in the art (see, e.g., Remington: The Science and Practice of Pharmacy (2003) 20th ed., Mack Publishing Co., Easton, Pa.; Remington's Pharmaceutical Sciences (1990) 18th ed., Mack Publishing Co., Easton, Pa.; The Merck Index (1996) 12th ed., Merck Publishing Group, Whitehouse, N.J.; Pharmaceutical Principles of Solid Dosage Forms (1993), Technomic Publishing Co., Inc., Lancaster, Pa.; Ansel and Stoklosa, Pharmaceutical Calculations (2001) 11th ed., Lippincott Williams & Wilkins, Baltimore, Md.; and Poznansky et al., Drug Delivery Systems (1980), R. L. Juliano, ed., Oxford, N.Y., pp. 253-315).

Compounds of the disclosure (e.g., CSAs), including pharmaceutical formulations can be packaged in unit dosage forms for ease of administration and uniformity of dosage. A "unit dosage form" as used herein refers to a physically discrete unit suited as unitary dosages for the subject to be administered or contacted; each unit containing a predetermined quantity of compound optionally in association with a pharmaceutical carrier (excipient, diluent, vehicle or filling agent). Unit dosage forms can contain a daily dose or unit, daily sub-dose, or an appropriate fraction thereof, of an administered compound (e.g., CSA). Unit dosage forms also include, for example, capsules, troches, cachets, lozenges, tablets, ampules and vials, which may include a composition in a freeze-dried or lyophilized state; a sterile liquid carrier, for example, can be added prior to administration, contact, or delivery in vivo. Unit dosage forms additionally include, for example, ampules and vials with liquid compositions disposed therein. Unit dosage forms further include compounds for transdermal administration, such as "patches" that contact with the epidermis of the subject for an extended or brief period of time. The individual unit dosage forms can be included in multi-dose kits or containers. Pharmaceutical formulations can be packaged in single or multiple unit dosage forms for ease of administration and uniformity of dosage.

Compounds of the disclosure (e.g., CSAs) can be administered at any duration or frequency. Typically, a labeled CSA is administered as a bolus or is administered in multiple dose to provide detection, diagnosis, screening or imaging.

Exemplary non-limiting doses include, for example, those based on the mass of a subject. Doses can generally be in a range from about 0.1-1 ug/kg, 1-10 ug/kg, 10-25 ug/kg, 25-50 ug/kg, 50-100 ug/kg, 100-500 ug/kg, 500-1,000 ug/kg, 1-4 mg/kg, 4-10 mg/kg, 10-20 mg/kg, 20-50 mg/kg, 50-100 mg/kg, 100-250 mg/kg, 250-500 mg/kg, or more, of subject body weight, two, three, four, or more times per hour, day, week, month or annually. Of course, doses can be more or less, as appropriate, for example, 0.00001 mg/kg of subject body weight to about 10,000.0 mg/kg of subject body weight, about 0.001 mg/kg, to about 100 mg/kg, about 0.01 mg/kg, to about 10 mg/kg, or about 0.1 mg/kg, to about 1 mg/kg of subject body weight over a given time period, e.g., 1, 2, 3, 4, 5 or more hours, days, weeks, months, years. A subject may be administered single bolus or in divided/metered doses, which can be adjusted to be more or less according to the various consideration set forth herein and known in the art. Dosage levels of labeled CSA also can take, into consideration the particular detectable label and detection system in order to achieve a desired image.

Kits

The disclosure provides kits including compounds of the disclosure (e.g., CSA), combination compositions and pharmaceutical compositions/formulations thereof, packaged into a suitable packaging material. In one embodiment, a kit includes packaging material, a cationic steroid antimicrobial (CSA) and instructions. In various aspects, the instructions are for administering the CSA to diagnose, detect, screen or image an infection.

The term "packaging material" refers to a physical structure housing one or more components of the kit. The packaging material can maintain the components sterilely, and can be made of material commonly used for such purposes (e.g., paper, corrugated fiber, glass, plastic, foil, ampules, vials, tubes, etc.). A kit can contain a plurality of components, e.g., two or more CSAs of the disclosure alone or in combination.

A kit optionally includes a label or insert including a description of the components (type, amounts, doses, etc.), instructions for use in vitro, in vivo, or ex vivo, and any other components therein. Labels or inserts include "printed matter," e.g., paper or cardboard, or separate or affixed to a component, a kit or packing material (e.g., a box), or attached to an ampule, tube or vial containing a kit component. Labels or inserts can additionally include a computer readable medium, such as a disk (e.g., hard disk, ZIP disk), optical disk such as CD- or DVD-ROM/RAM, DVD, MP3, magnetic tape, or an electrical storage media such as RAM and ROM or hybrids of these such as magnetic/optical storage media, FLASH media or memory type cards.

Labels or inserts can include identifying information of one or more components therein, dose amounts, clinical pharmacology of the active ingredient(s) including mechanism of action, pharmacokinetics and pharmacodynamics. Labels or inserts can include information identifying manufacturer, lot numbers, manufacturer location and date, expiration dates.

Labels or inserts can include information on an infection, disorder or disease (e.g., bacterial or virus infection) for which a kit component may be used. Labels or inserts can include instructions for a clinician or subject for using one or more of the kit components in a method, treatment protocol or therapeutic/prophylactic regimen, including the methods of the disclosure. Instructions can include amounts of compound, frequency or duration of administration, and instructions for practicing any of the methods, treatment protocols or prophylactic or therapeutic regimes described herein. Kits therefore can additionally include labels or instructions for practicing any of the methods of the disclosure described herein including detection, diagnosis, screening or other methods.

Kits can additionally include a buffering agent, or a preservative or a stabilizing agent in a pharmaceutical formulation containing a compound of the disclosure. Each component of the kit can be enclosed within an individual container and all of the various containers can be within a single package. Kits can be designed for cold storage.

All of the features disclosed herein may be combined in any combination. Each feature disclosed in the specification may be replaced by an alternative feature serving a same, equivalent, or similar purpose. Thus, unless expressly stated otherwise, disclosed features (e.g., compound structures) are an example of a genus of equivalent or similar features.

A number of embodiments of the disclosure have been described. Nevertheless, one skilled in the art, without departing from the spirit and scope of the disclosure, can make various changes and modifications of the disclosure to adapt it to various usages and conditions. For example, salts, esters, ethers and amides of disclosure compounds disclosed herein are within the scope of this disclosure. Accordingly, the following examples are intended to illustrate but not limit the scope of disclosure described in the claims.

EXAMPLES

Examples 1A and 1B $^{64}$CuCl diluted with a ten-fold excess of 0.1 M ammonium acetate (NH$_4$OAc) at a pH of approximately 5.5 was reacted with CSA-150 (Example 1A) and CSA-151 (Example 1B). Labeling of the compounds achieved a purity >98%, which was observed using HPLC (Phenomenex C-18 Kinetex 5 μm, 4.6×150 mm analytical column with a 0.1% TFA water-acetonitrile gradient elution). Chromatograms showing the results of the labeling example are shown in FIG. 1.

Examples 2A and 2B

The specific activities of the labeled CSA-150 and CSA-151 compounds of Example 1 were measured. Specific activity achieved a level of 100 μCi/μg for both labeled CSA-150 (Example 2A) and labeled CSA-151 (Example 2B).

Examples 3A and 3B

Stability of the labeled CSA-150 and CSA-151 compounds of Example 1 was measured. The labeled compounds were placed in human serum for four hours at 37 degrees C. at 500 rpm incubation. Both of the labeled CSA-150 (Example 3A) and CSA-151 (Example 3B) compounds were found to be 100% stable after the four hour period.

Examples 4A and 4B

Figure 2:
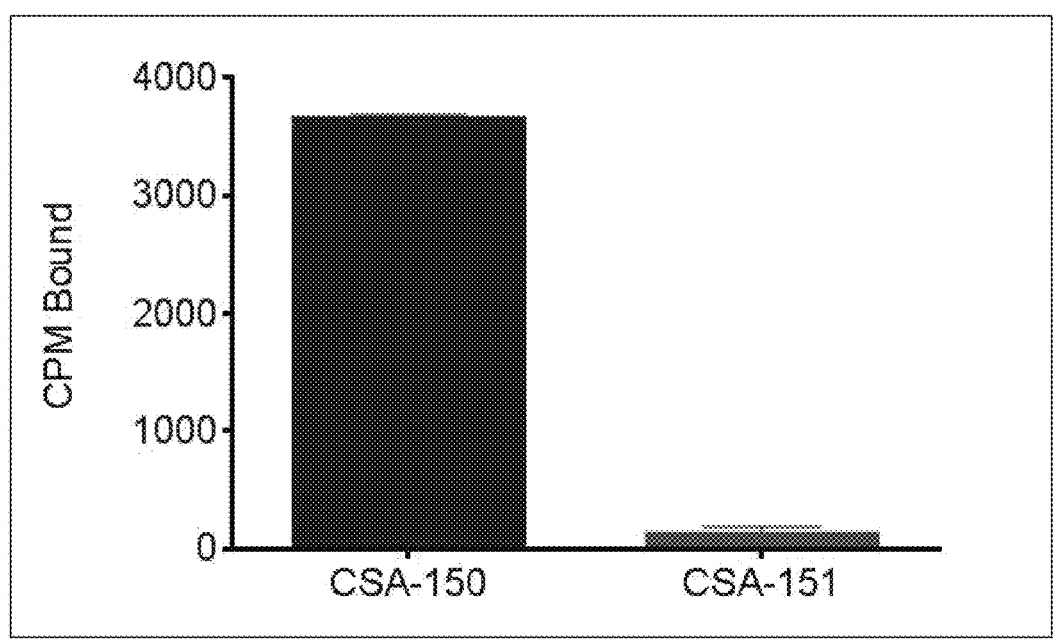
FIG. 2 shows in vitro cell binding of a labeled CSA-150 compound and a labeled CSA-151 compound.

Labeled CSA-150 (Example 4A) and CSA-151 (Example 4A) from Examples 1A and 2B were used in a binding study conducted with *Escherichia Coli* strain W1485 to verify the interactions of these ceragenins with bacterial cell membranes. The $^{64}$Cu labeled compounds were incubated at room temperature with 1×10$^6$ cells for one hour. After a phosphate buffered saline (PBS) wash, cell activity was measured. The results of this example are shown in FIG. 2.

Examples 5A and 5B

Figure 3:
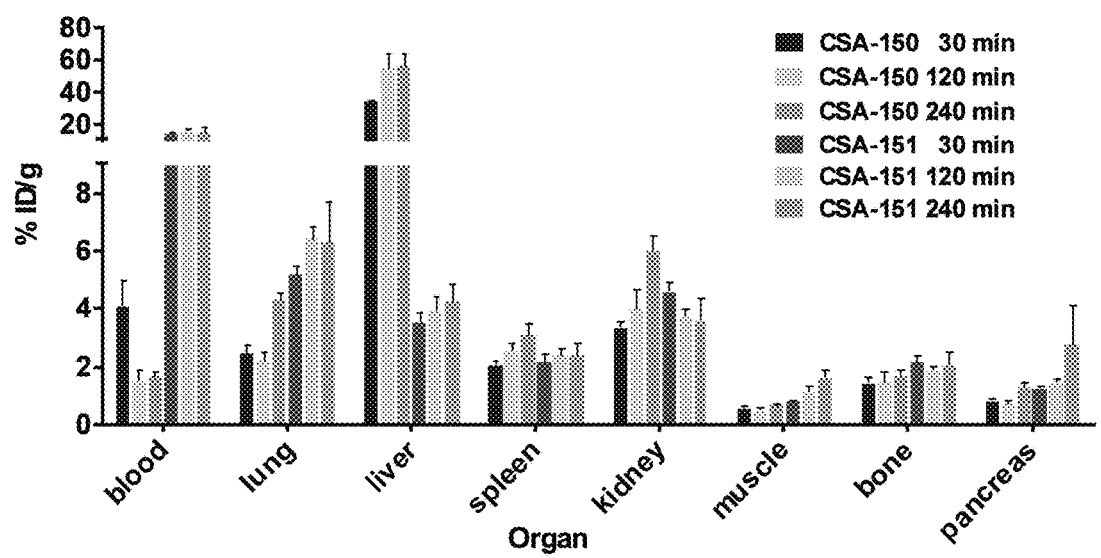
FIG. 3 shows in vivo biodistribution of a labeled CSA-150 compound and a labeled CSA-151 compound.
Figure 4:
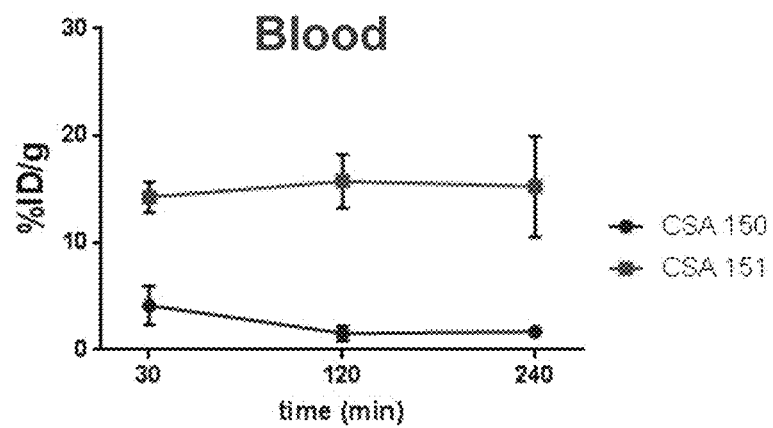
FIG. 4 shows in vivo biodistribution of a labeled CSA-150 compound and a labeled CSA-151 compound in mouse blood over time.
Figure 5:
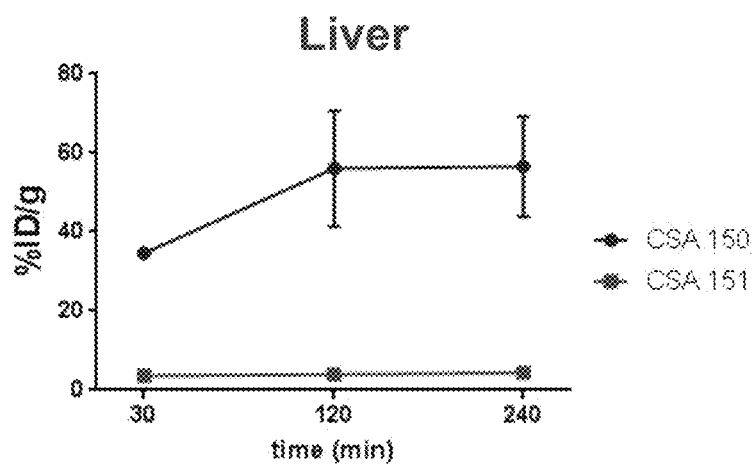
FIG. 5 shows in vivo biodistribution of a labeled CSA-150 compound and a labeled CSA-151 compound in mouse liver tissue over time.
Figure 6:
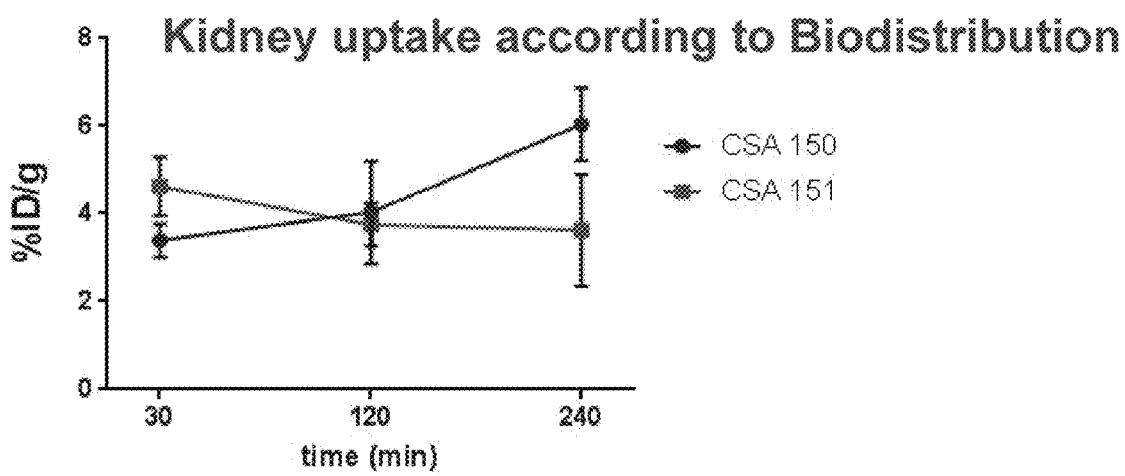
FIG. 6 shows in vivo biodistribution of a labeled CSA-150 compound and a labeled CSA-151 compound in mouse kidney tissue over time.

An in vivo biodistribution study was done using the labeled CSA-150 and CSA-151 compounds of Examples 1A and 1B. 10 μCi of $^{64}$Cu labeled ceragenins (100 μL in 10% NH$^4$OAc and 90% saline) was injected into CD-1 mice (20-25 g, female, n=4). The mice were sacrificed at 30 minutes, two hours, and four hours post injection, and organs of interest were removed and analyzed for activity. FIG. 3 shows the contrasting uptake of the CSA-150 (Example 5A) and the CSA-151 (Example 5B) control in various organs. FIG. 4 shows the contrasting uptake of the CSA-150 and the CSA-151 control in mouse blood over time. FIG. 5 shows the contrasting uptake of the CSA-150 and the CSA-151 control in mouse liver tissue over time. FIG. 6 shows the contrasting uptake of the CSA-150 and the CSA-151 control in mouse kidney tissue overtime.

Examples 6A and 6B

Figure 7:
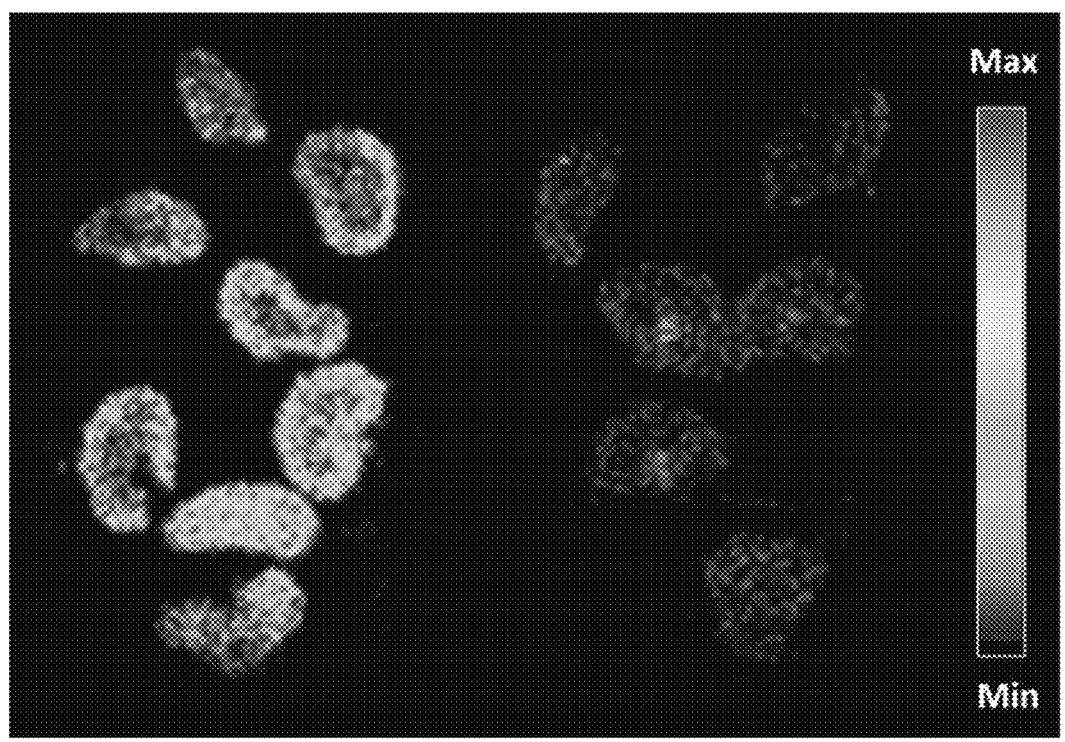
FIG. 7 shows ex vivo autoradiography imaging of mouse kidney sections containing labeled CSA-150 compound or labeled CSA-151 compound at two hours post injection.
Figure 8:
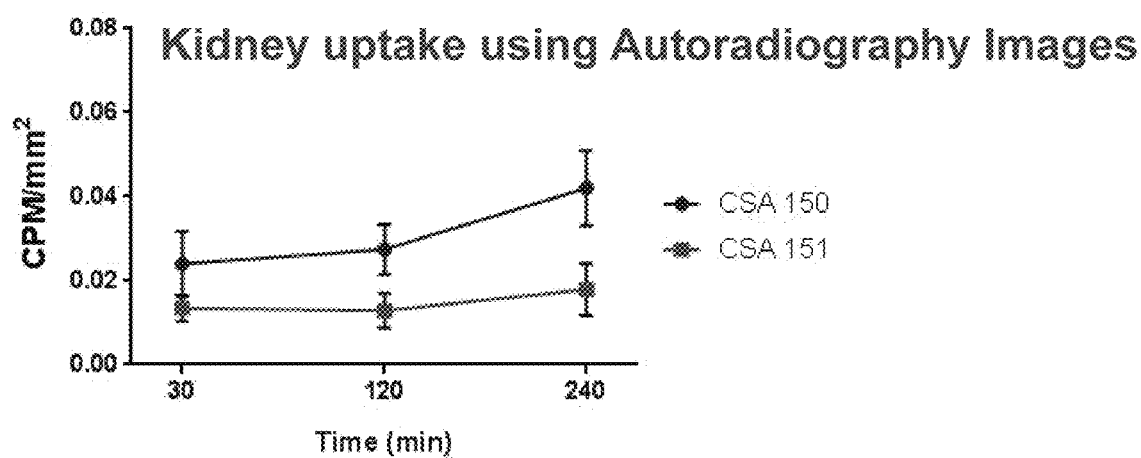
FIG. 8 shows mouse kidney uptake of a labeled CSA-150 compound and a labeled CSA-151 compound based on autoradiography imaging.
Figure 9:
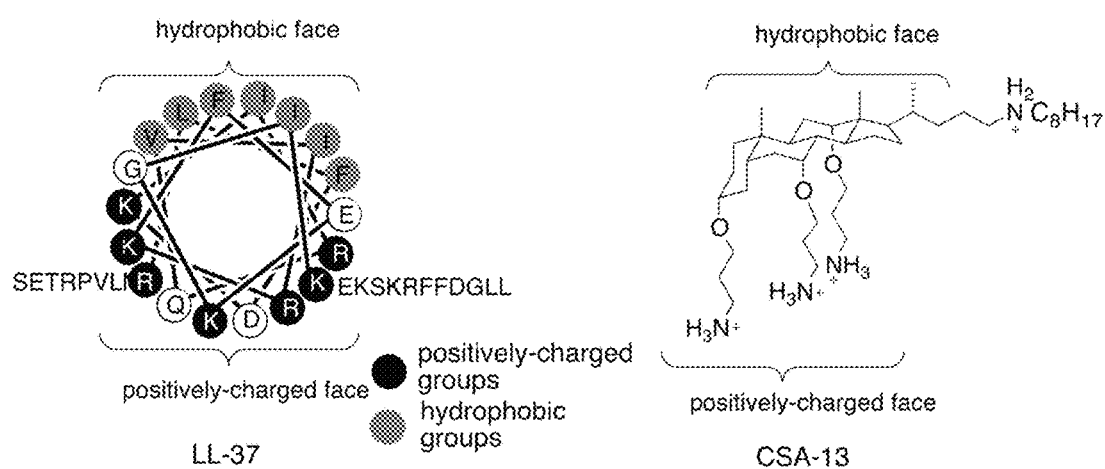
FIG. 9 schematically depicts the antimicrobial peptide LL-37 and the ceragenin CSA-13.

Kidney tissue samples from Examples 5A and 5B were analyzed using ex vivo autoradiography imaging. Organ samples were collected for freezing at 30 minutes, two hours, and four hours post injection. The samples were sliced to 20-40 μm sections using a Vibratome 8850. Sliced sections were then exposed to a phosphor imaging screen for 12 hours at −20 degrees C. in an imaging cassette. 50 micron scans were conducted using a phosphor imager plate scanner (Storm 840). Scans were analyzed using ImageQuant 5.2 software (Molecular Dynamics). FIG. 7 shows an autoradiography image of the kidney slices at two hours post injection, with the CSA-150 treated samples on the left (Example 6A) and the CSA-151 control treated samples on the right (Example 6B). FIG. 8 shows kidney uptake of the labeled CSA-150 compound and the labeled CSA-151 control based on analysis of the autoradiography images.

The present invention may be embodied in other specific forms without departing from its spirit or essential characteristics. The described embodiments are to be considered in all respects only as illustrative and not restrictive. The scope of the invention is, therefore, indicated by the appended claims rather than by the foregoing description. All changes which come within the meaning and range of equivalency of the claims are to be embraced within their scope. Additionally, the elements and components of the embodiments disclosed herein may be combined and/or substituted, and are not intended to be confined to any particular embodiment.

The invention claimed is:

1. A cationic steroidal antimicrobial (CSA) compound of Formula III, or salt thereof:

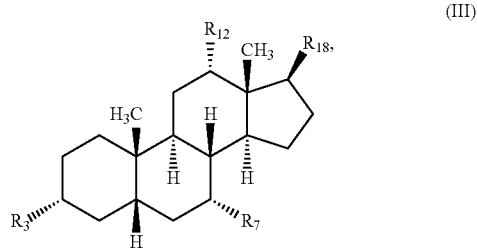

(III)

wherein, $R_3$, $R_7$, and $R_{12}$ are independently selected from the group consisting of hydrogen, unsubstituted ($C_1$-$C_6$) alkyl, unsubstituted ($C_1$-$C_6$) hydroxyalkyl, unsubstituted ($C_1$-$C_{16}$) alkyloxy-($C_1$-$C_5$) alkyl, unsubstituted ($C_1$-$C_{16}$) alkylcarboxy-($C_1$-$C_5$) alkyl, unsubstituted ($C_1$-$C_{16}$) alkylamino-($C_1$-$C_5$)alkyl, unsubstituted ($C_1$-$C_{16}$) alkylamino-($C_1$-$C_5$) alkylamino, unsubstituted ($C_1$-$C_{16}$) alkylamino-($C_1$-$C_{16}$) alkylamino-($C_1$-$C_5$) alkylamino, unsubstituted ($C_1$-$C_{16}$) aminoalkyl, unsubstituted arylamino-($C_1$-$C_5$) alkyl, unsubstituted ($C_1$-$C_5$) aminoalkyloxy, unsubstituted ($C_1$-$C_{16}$) aminoalkyloxy-($C_1$-$C_5$) alkyl, unsubstituted ($C_1$-$C_5$) aminoalkylcarboxy, unsubstituted ($C_1$-$C_5$) aminoalkylaminocarbonyl, unsubstituted ($C_1$-$C_5$) aminoalkylcarboxamido, unsubstituted di($C_1$-$C_5$ alkyl)amino-($C_1$-$C_5$) alkyl, unsubstituted ($C_1$-$C_5$) guanidinoalkyloxy, unsubstituted ($C_1$-$C_{16}$) quaternary ammonium alkylcarboxy, and unsubstituted ($C_1$-$C_{16}$) guanidinoalkylcarboxy, wherein 0 or 1 of $R_3$, $R_7$, and $R_{12}$ is hydrogen; and $R_{18}$ is

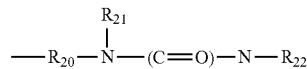

wherein, $R_{20}$ is an alkyl, alkenyl, alkynyl, or aryl connected to $R_{22}$ by a urea;

$R_{21}$ is selected from the group consisting of hydrogen, $C_1$-$C_{24}$ alkyl, $C_2$-$C_{24}$ alkenyl, $C_2$-$C_{24}$ alkynyl, $C_7$-$C_{13}$ aralkyl, $C_1$-$C_6$ alkyl-(5 to 10 membered heteroaryl), $C_3$-$C_{10}$ carbocyclyl, $C_4$-$C_{10}$ (carbocyclyl) alkyl, and amido; and $R_{22}$ is a heterocyclic ring chelator having at least 2 heteroatoms and being attached to the urea by a linkage selected from the group consisting of alkyl, -[alkoxy]$_n$, -[alkoxy]$_n$-alkyl, alkylcarboxamido-alkyl, alkylcarboxamido-[alkoxy]$_n$, alkylcarboxamido-[alkoxy]$_n$-alkyl, alkylcarboxyalkyl, alkylaminoalkyl, aryl, arylaminoalkyl, alkenyl, and alkynyl, where n is 1 to 10, wherein each of $R_{20}$, $R_{21}$, and $R_{22}$ may be optionally substituted, and wherein the heterocyclic ring chelator is spaced apart from the steroidal backbone by a linkage having at least 10 atoms.

2. The CSA compound of claim 1, wherein the heterocyclic ring chelator is selected from the group consisting of: 1,4,7-triazacyclononane-N,N',N"-triacetic acid (NOTA), 1,4,7-triazacyclodecane-N,N',N"-triacetic acid (DETA), 1,4,8-triazacycloundecane-N,N',N"-triacetic acid (UNTA), 1,5,9-triazacyclododecane-N,N',N"-triacetic acid (DOTRA), 9,10-benzylidene-1,4,7-triazacyclotridecane-N,N',N"-triacetic acid (BUNTA), and 1,4,7,10-tetraazacyclododecane-1,4,7,10-tetracetic acid (DOTA).

3. The CSA compound of claim 1, wherein the heterocyclic ring chelator is spaced apart from the steroidal backbone by a linkage having at least 12 atoms.

4. The CSA compound of claim 1, wherein the heterocyclic ring chelator is spaced apart from the steroidal backbone by a linkage having at least 16 atoms.

5. The CSA compound of claim 1, wherein the heterocyclic ring chelator is spaced apart from the steroidal backbone by a linkage having at least 20 atoms.

6. The CSA compound of claim 1, wherein the heterocyclic ring chelator is spaced apart from the steroidal backbone by a linkage having at least 24 atoms.

7. The CSA compound of claim 1, wherein the heterocyclic ring chelator is a 5 to 13 member ring.

8. The CSA compound of claim 1, wherein the heterocyclic ring chelator is an 8 to 12 member ring.

9. The CSA compound of claim 1, wherein the heterocyclic ring chelator is a 9-10 member ring.

10. The CSA compound of claim 1, wherein $R_3$, $R_7$, and $R_{12}$ are independently selected from the group consisting of aminoalkyloxy; aminoalkylcarboxy; alkylaminoalkyl; alkoxycarbonylalkyl; alkylcarbonylalkyl; di(alkyl)aminoalkyl; alkylcarboxyalkyl; and hydroxyalkyl.

11. The CSA compound of claim 1, wherein $R_3$, $R_7$, and $R_{12}$ are independently selected from the group consisting of aminoalkyloxy and aminoalkylcarboxy.

12. The CSA compound of claim 1, wherein $R_3$, $R_7$, and $R_{12}$ are the same.

13. The CSA compound of claim 1, wherein $R_3$, $R_7$, and $R_{12}$ are independently selected from the group consisting of amino-$C_3$-alkyloxy; amino-$C_3$-alkyl-carboxy; $C_8$-alkylamino-$C_5$-alkyl; $C_8$-alkoxy-carbonyl-$C_4$-alkyl; $C_8$-alkylcarbonyl-$C_4$-alkyl; di-($C_5$-alkyl)amino-$C_5$-alkyl; $C_{13}$-alkylamino-$C_5$-alkyl; $C_6$-alkoxy-carbonyl-$C_4$-alkyl; $C_6$-alkylcarboxy-$C_4$-alkyl; and $C_{16}$-alkylamino-$C_5$-alkyl.

14. The CSA compound of claim 1, wherein the CSA compound is (CSA-153)

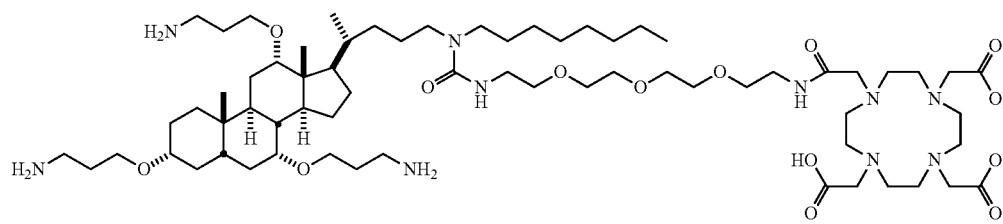

or salts thereof.

15. The CSA compound of claim 1, further comprising a detectable label that is $^{64}$Cu.

16. The CSA compound of claim 1, further comprising a detectable label that is a metal crystal or metal oxide crystal.

17. The CSA compound of claim 1, further comprising a detectable label that is selected from the group consisting of: gold, silver, copper, boron, manganese, gadolinium, iron, chromium, barium, europium, erbium, praseodymium, indium, and technetium.

18. The CSA compound of claim 1, further comprising a detectable label that is a metal oxide selected from the group consisting of: Gd(III), Mn(II), Mn(III), Cr(II), Cr(III), Cu(II), Fe(III), Pr(III), Nd(III) Sm(III), Tb(III), Yb(III) Dy(III), Ho(III), Eu(II), Eu(III), or Er(III).

19. A cationic steroidal antimicrobial (CSA) compound of Formula III, or salt thereof:

(III)

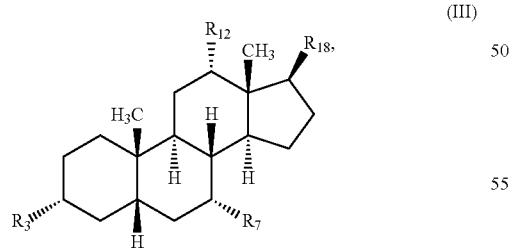

wherein, $R_3$, $R_7$, and $R_{12}$ are independently selected from the group consisting of hydrogen, unsubstituted ($C_1$-$C_6$) alkyl, unsubstituted ($C_1$-$C_6$) hydroxyalkyl, unsubstituted ($C_1$-$C_{16}$) alkyloxy-($C_1$-$C_5$) alkyl, unsubstituted ($C_1$-$C_{16}$) alkylcarboxy-($C_1$-$C_5$) alkyl, unsubstituted ($C_1$-$C_{16}$) alkylamino-($C_1$-$C_5$)alkyl, unsubstituted ($C_1$-$C_{16}$) alkylamino-($C_1$-$C_5$) alkylamino, unsubstituted ($C_1$-$C_{16}$) alkylamino-($C_1$-$C_{16}$) alkylamino-($C_1$-$C_5$) alkylamino, unsubstituted ($C_1$-$C_{16}$) aminoalkyl, unsubstituted arylamino-($C_1$-$C_5$) alkyl, unsubstituted ($C_1$-$C_5$) aminoalkyloxy, unsubstituted ($C_1$-$C_{16}$) aminoalkyloxy-($C_1$-$C_5$) alkyl, unsubstituted ($C_1$-$C_5$) aminoalkylcarboxy, unsubstituted ($C_1$-$C_5$) aminoalkylaminocarbonyl, unsubstituted ($C_1$-$C_5$) aminoalkylcarboxamido, unsubstituted di($C_1$-$C_5$ alkyl)amino-($C_1$-$C_5$) alkyl, unsubstituted ($C_1$-$C_5$) guanidinoalkyloxy, unsubstituted ($C_1$-$C_{16}$) quaternary ammonium alkylcarboxy, and unsubstituted ($C_1$-$C_{16}$) guanidinoalkylcarboxy, wherein 0 or 1 of $R_3$, $R_7$, and $R_{12}$ is hydrogen; and $R_{18}$ has the following structure:

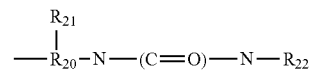

wherein, $R_{20}$ is an alkyl, alkenyl, alkynyl, or aryl connected to $R_{22}$ by a urea;

$R_{21}$ is selected from the group consisting of hydrogen, $C_1$-$C_{24}$ alkyl, $C_2$-$C_{24}$ alkenyl, $C_2$-$C_{24}$ alkynyl, $C_7$-$C_{13}$ aralkyl, $C_1$-$C_6$ alkyl-(5 to 10 membered heteroaryl), $C_3$-$C_{10}$ carbocyclyl, $C_4$-$C_{10}$ (carbocyclyl) alkyl, and amido; and $R_{22}$ is a 5 to 13 member, 8 to 12 member, or 9 to 10 member heterocyclic ring attached to the urea by a linkage selected from the group consisting of alkyl, -[alkoxy]$_n$-, -[alkoxy]$_n$-alkyl, alkylcarboxamido-alkyl, alkylcarboxamido-[alkoxy]$_n$, alkylcarboxamido-[alkoxy]$_n$-alkyl, alkylcarboxyalkyl, alkylaminoalkyl, aryl, arylaminoalkyl, alkenyl, and alkynyl, where n is 1 to 10, wherein the heterocyclic ring is selected from triazamacrocyclic ring and tetraazamacrocyclic ring, wherein each of $R_{20}$, $R_{21}$, and $R_{22}$ may be optionally substituted, and wherein the heterocyclic ring is spaced apart from the steroidal backbone by a linkage having at least 14 atoms, the CSA compound further comprising a detectable label, the detectable label comprising a metal or metal compound bound or complexed to the heterocyclic ring.

20. A cationic steroidal antimicrobial (CSA) compound selected from the group consisting of:

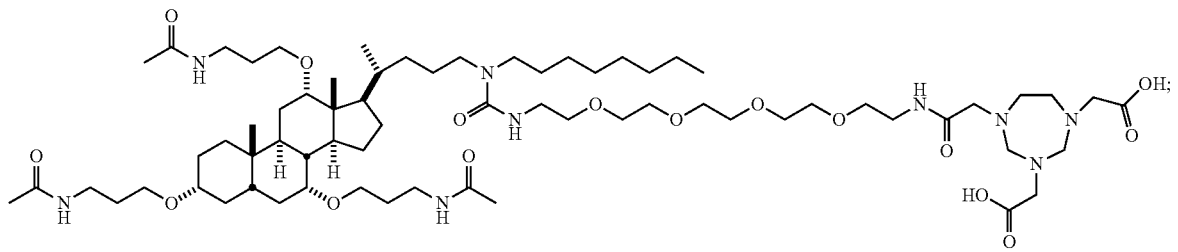

(CSA-150)

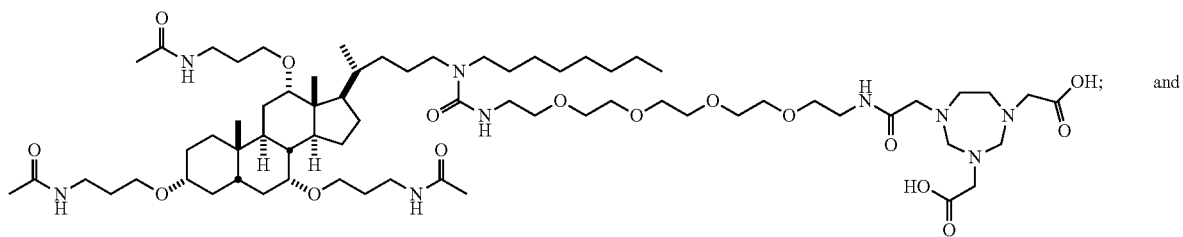

(CSA-151)

and

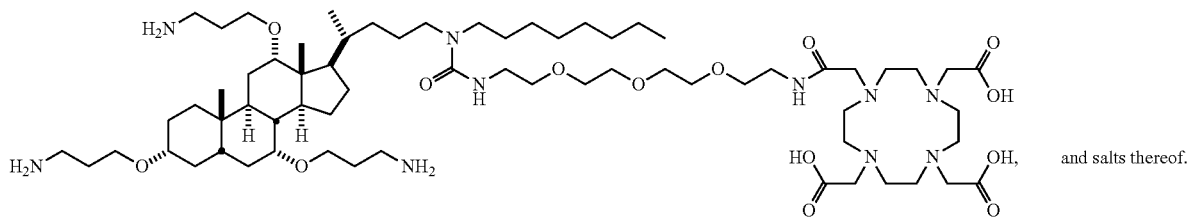

(CSA-153)

and salts thereof.

21. The CSA compound of claim 1, wherein the heterocyclic ring chelator is spaced apart from the urea by 1 to 6 ether moieties.

22. The CSA compound of claim 1, wherein the heterocyclic ring chelator is spaced apart from the urea by 3 ether moieties.

23. The CSA compound of claim 1, wherein the heterocyclic ring chelator is spaced apart from the urea by 4 ether moieties.

24. The CSA compound of claim 19, wherein the heterocyclic ring is spaced apart from the urea by 1 to 6 ether moieties.

25. The CSA compound of claim 19, wherein the heterocyclic ring is spaced apart from the urea by 3 ether moieties.

26. The CSA compound of claim 19, wherein the heterocyclic ring is spaced apart from the urea by 4 ether moieties.

* * * * *